United States Patent
Perlingeiro et al.

(10) Patent No.: US 11,697,798 B2
(45) Date of Patent: Jul. 11, 2023

(54) ENHANCED DIFFERENTIATION AND MATURATION OF PLURIPOTENT STEM CELL-DERIVED MYOGENIC CELLS

(71) Applicant: Regents of the University of Minnesota, Minneapolis, MN (US)

(72) Inventors: Rita Perlingeiro, St. Paul, MN (US); Sridhar Selvaraj, Minneapolis, MN (US); Ricardo Mondragon Gonzalez, Estado de Mexico (MX)

(73) Assignee: Regents of the University of Minnesota, Minneapolis, MN (US)

( * ) Notice: Subject to any disclaimer, the term of this patent is extended or adjusted under 35 U.S.C. 154(b) by 353 days.

(21) Appl. No.: 16/770,917

(22) PCT Filed: Dec. 13, 2018

(86) PCT No.: PCT/US2018/065531
§ 371 (c)(1),
(2) Date: Jun. 8, 2020

(87) PCT Pub. No.: WO2019/118768
PCT Pub. Date: Jun. 20, 2019

(65) Prior Publication Data
US 2021/0171911 A1 Jun. 10, 2021

Related U.S. Application Data
(60) Provisional application No. 62/598,200, filed on Dec. 13, 2017.

(51) Int. Cl.
*C12N 5/077* (2010.01)
(52) U.S. Cl.
CPC ...... *C12N 5/0658* (2013.01); *C12N 2501/999* (2013.01); *C12N 2506/02* (2013.01); *C12N 2506/45* (2013.01)

(58) Field of Classification Search
CPC .................................................... C12N 5/0658
See application file for complete search history.

(56) References Cited

U.S. PATENT DOCUMENTS

| | | | | |
|---|---|---|---|---|
| 2011/0158960 A1* | 6/2011 | Luyten | ............... | A61L 27/3886 424/93.7 |
| 2015/0147807 A1* | 5/2015 | Zon | .................... | A61K 38/1808 435/377 |

FOREIGN PATENT DOCUMENTS

| | | | | |
|---|---|---|---|---|
| WO | WO-2016137400 A1 * | 9/2016 | ........... | C12N 5/0658 |
| WO | WO-2017100498 A1 | 6/2017 | | |

(Continued)

OTHER PUBLICATIONS

Horbelt et al. "Small Molecules Dorsomorphin and LDN-193189 Inhibit Myostatin/GDF8 Signaling and Promote Functional Myoblast Differentiation" vol. 290, No. 6, Feb. 6, 2015. (Year: 2015).*

(Continued)

*Primary Examiner* — Marcia S Noble
*Assistant Examiner* — Lauren K Van Buren
(74) *Attorney, Agent, or Firm* — Schwegman Lundberg & Woessner, P.A.

(57) ABSTRACT

A method to increase the efficiency of myotube generation and maturation from pluripotent stem cells comprising: (a) differentiating pluripotent stem cells to myogenic progenitors; and (b) terminally differentiating said myogenic progenitors from (a) into myotubes in the presence of at least one gamma secretase inhibitor, wherein myotube generation is increased in the presence of at least one gamma secretase inhibitor, as compared to differentiation in the absence of gamma secretase inhibitors.

8 Claims, 29 Drawing Sheets

(56) References Cited

FOREIGN PATENT DOCUMENTS

| WO | WO-2017196175 A1 | 11/2017 |
| WO | WO-2019118768 A1 | 6/2019 |

OTHER PUBLICATIONS

David et al. "Isolation and purification of myotube and myoblast nuclei from cultures of embryonic chick skeletal muscle" Experimental Cell Research, vol. 117, Issue 1, Nov. 1978, pp. 63-70. (Year: 1978).*

Lee et al. "Inhibition of pluripotent stem cell-derived teratoma formation by small molecules" PNAS, Published online Aug. 5, 2013, E3281-E3290. (Year: 2013).*

Moon et al. "Differentiation of hESCs into Mesodermal Subtypes: Vascular, Hematopoietic, and Mesenchymal Lineage Cells" International Journal of Stem Cells, vol. 4, No. 1, 2011 (Year: 2011).*

Sylvester et al. "Stem Cells" Arch Surg/vol. 139, Jan. 2004 (Year: 2004).*

"International Application Serial No. PCT/US2018/065531, International Search Report dated Feb. 27, 2019", 3 pgs.

"International Application Serial No. PCT/US2018/065531, Written Opinion dated Feb. 27, 2019", 3 pgs.

Mu, X, et al., "The Role of Notch Signaling in Muscle Progenitor Cell Depletion and the Rapid Onset of Histopathology in Muscular Dystrophy", Human Molecular Genetics, vol. 24, No. 10, (May 15, 2015), 2923-2937.

"International Application Serial No. PCT/US2018/065531, International Preliminary Report on Patentability dated Jun. 25, 2020", 8 pgs.

Barberi, Tiziano, et al., "Derivation of engraftable skeletal myoblasts from human embryonic stem cells", Nature Medicine, 13(5), (Jun. 2007), 642-648.

Black III, Lauren, et al., "Cell-Induced Alignment Augments Twitch Force in Fibrin Gel-Based Engineered Myocardium", Tissue Engineering: Part A, vol. 15, No. 10, (2009), 3099-3108.

Borchin, Bianca, et al., "Derivation and FACS-Mediated Purification of PAX3+/PAX7+ Skeletal Muscle Precursors from Human Pluripotent Stem Cells", Stem Cell Reports, vol. 1, (2013), 620-631.

Chal, Jerome, et al., "Making muscle: skeletal myogenesis in vivo and in vitro", Development, 144, (2017), 2104-2122.

Darabi, Radbod, et al., "Derivation of Skeletal Myogenic Precursors from Human Pluripotent Stem Cells Using Conditional Expression of PAX7", Methods Mol Biol,, 1357, (2016), 423-439.

Darabi, Radbod, et al., "Human ES-and IPS-Derived Myogenic Progenitors Restore Dystrophin and Improve Contractility upon Transplantation in Dystrophic Mice", Cell Stem Cell, 10(5), (2012), 610-619.

Dovey, H. F., et al., "Functional gamma-secretase inhibitors reduce beta-amyloid peptide levels in brain", Journal of Neurochemistry, 76(1), (2001), 173-181.

Gavai, Ashvinikumar, et al., "Discovery of Clinical Candidate BMS-906024: A Potent Pan-Notch Inhibitor for the Treatment of Leukemia and Solid Tumors", ACS Medicinal Chemistry Letters, 6, (2015), 523-527.

Kim, Jaemin, et al., "Expansion and Purification Are Critical for the Therapeutic Application of Pluripotent Stem Cell-Derived Myogenic Progenitors", Stem Cell Reports, 9(1), (2017), 12-22.

Shelton, Michael, et al., "Derivation and Expansion of PAX7-Positive Muscle Progenitors from Human and Mouse Embryonic Stem Cells", Stem Cell Reports, vol. 3, (2014), 516-529.

Xi, et al., "In Vivo Human Somitogenesis Guides Somite Development from hPSCs", Cell Reports, 18, (2017), 1573-1585.

Young, Courtney S., et al., "A Single CRISPR-Cas9 Deletion Strategy that Targets the Majority of DMD Patients Restores dystrophin Function in hiPSC-Derived Muscle Cells", Cell Stem Cell, 18(4), (2016), 533-540.

* cited by examiner

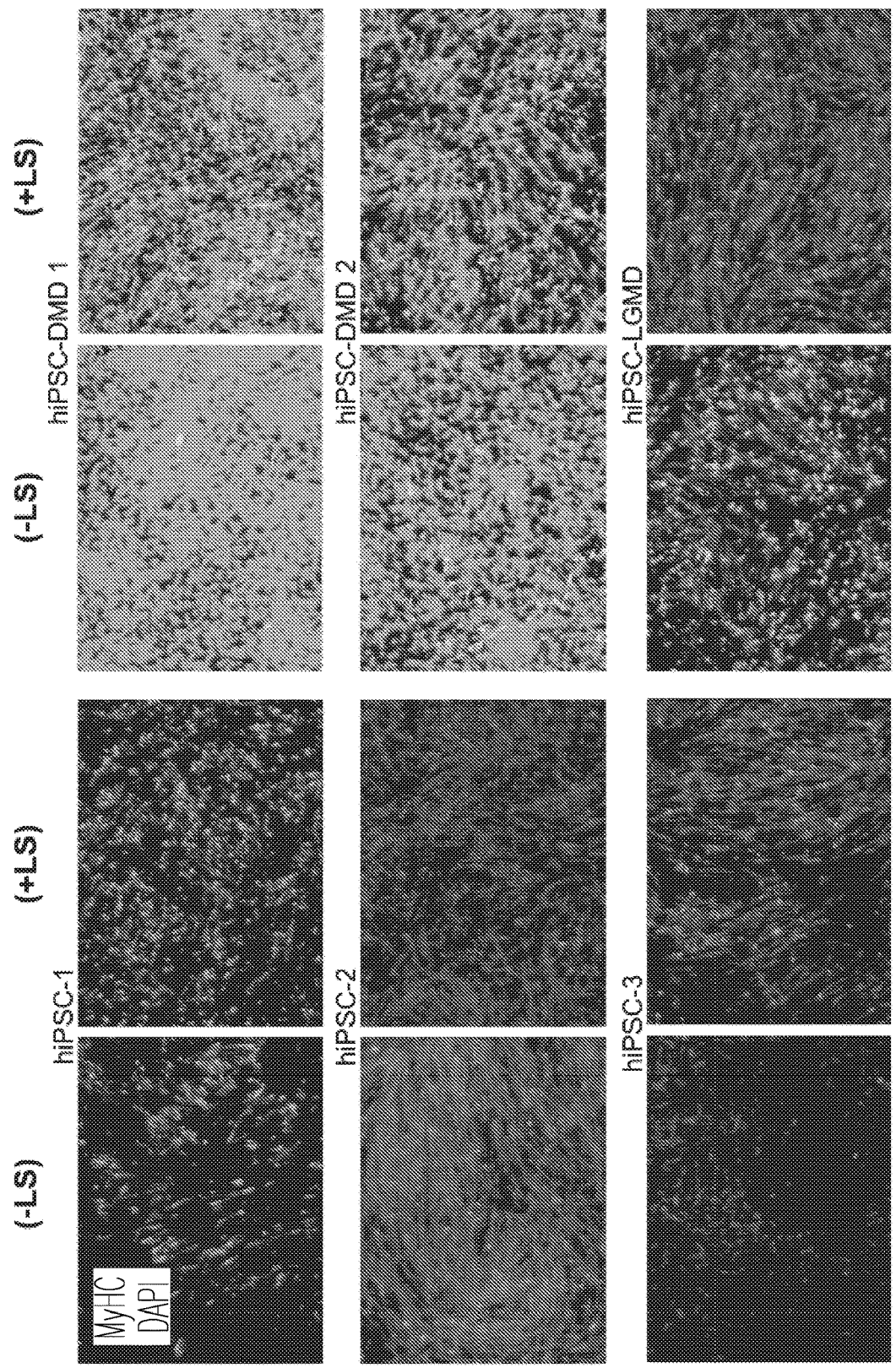

ENHANCED DIFFERENTIATION AND MATURATION OF PLURIPOTENT STEM CELL-DERIVED MYOGENIC CELLS

PRIORITY

This application is a U.S. National Stage Application under 35 U.S.C. 371 from International Application Serial No. PCT/US2018/065531, filed on Dec. 13, 2018, and published as WO 2019/118768 A1 and published on Jun. 2, 2019, which claims the benefit of priority from U.S. Provisional Patent Application Ser. No. 62/598,200, filed on Dec. 13, 2017, which is herein incorporated in its entirety by reference.

BACKGROUND OF THE INVENTION

Pluripotent stem cells represent an attractive model system for studying various genetic diseases due to their ability to differentiate in vitro into various cell types of the body. This feature also allows for studying disease mechanisms in vitro using patient-specific induced pluripotent stem (iPS) cells. One challenge encountered when using pluripotent stem cells, such as iPS cell-derivatives, to study diseases has been that pluripotent stem cells tend to produce embryonic, fetal, or generally immature forms of the terminally differentiated cell types desired (as reported for cardiomyocytes, hepatocytes, and pancreatic cells). The lack of full maturation of terminally differentiated cells, is a caveat for the application of iPS cell-derivatives for disease modeling.

SUMMARY OF INVENTION

Provided herein are compositions, methods and kits to enhance both the generation and the maturation of skeletal myocytes from differentiating stem cells.

The present invention provides methods to obtain myotubes comprising: (a) differentiating pluripotent stem cells into myogenic progenitors; (b) terminally differentiating said myogenic progenitors from (a) into myotubes in the presence of at least one gamma secretase inhibitor. It also provides a method by which myotubes produced in any manner may be pushed/differentiated towards a more mature state.

One embodiment provides a method to increase the efficiency of myotube generation from pluripotent stem cells comprising: (a) differentiating pluripotent stem cells into myogenic progenitors; and (b) terminally differentiating said myogenic progenitors from (a) into myotubes in the presence of at least one gamma secretase inhibitor, wherein myotube generation and maturation is increased, as compared to differentiation in the absence of gamma secretase inhibitors.

In one embodiment, the gamma secretase inhibitor is DAPT, BMS-906024 or a combination thereof.

One embodiment provides a method to screen for a compound that increases differentiation efficiency and/or maturation of myotubes generated from pluripotent stem cell-derived myogenic progenitors comprising: (a) differentiating pluripotent stem cells to myogenic progenitors; (b) terminally differentiated said myogenic progenitors from (a) into myotubes in the presence of a test compound; and (c) detect the presence of myotubes, wherein if there is an increase in myotube formation in the presence of said test compound, as compared to cells grown in the absence of said test compound, then said test compound is a compound that increases efficiency and/or maturation of myotubes generated from pluripotent stem cell-derived myogenic progenitors.

In one embodiment, the pluripotent stem cells are human induced pluripotent stem cells (hiPSC) or embryonic stem cells (hESC). In another embodiment, the mature myotubes have increased expression of MHC8 (as compared to cells not differentiated in the presence of an inhibitor/test compound).

In one embodiment, the pluripotent stem cells are genetically modified. In another embodiment, differentiating pluripotent stem cells to myogenic progenitors is carried out by inducible expression of PAX7.

Another embodiment provides a composition comprising myogenic progenitors and at least one gamma secretase inhibitor.

BRIEF DESCRIPTION OF THE DRAWINGS

FIGS. 6A-C. Inhibition of BMP and TGFβ signaling during embryoid body (EB)-iPAX7 myogenic differentiation protocol improves in vitro terminal differentiation and in vivo engraftment capabilities of resulting human iPS cell-derived myogenic progenitors. (A) Representative images of immunostaining of non-disease hiPS cells-derived myotubes (hiPSC-1, -2 and -3) and muscular dystrophy hiPS cells-derived myotubes (hiPSC-DMD 1, -DMD 2 and LGMD) differentiated following the EB-iPAX7 protocol with modifications to incorporate inhibition of BMP and TGFβ signaling (+LS) show increased MyHC staining (red) compared to control (−LS), particularly in cell lines with poor differentiation efficiency under (−LS) conditions. (B) Cryo-sections of tibialis anterior muscles of NSG mice transplanted with hiPSC-1-derived myogenic progenitors differentiated under (+LS) conditions were analyzed by immunostaining to identify engrafted cells, positive for human lamin A/C (hLMNA/C, green) and human dystrophin (hDYS, red). Images (i and ii) represent two fields within the same muscle section. Scale bar is 200 µm. (C) Quantification of engraftment (hLMNA/C+ and hDYS+) from (B). Sections with higher visible engraftment were used as reference (0) and sections obtained 220 µm from the reference point were quantified to get insights on the depth of the engraftment efficiency.

DETAILED DESCRIPTION OF THE INVENTION

Figure 1:
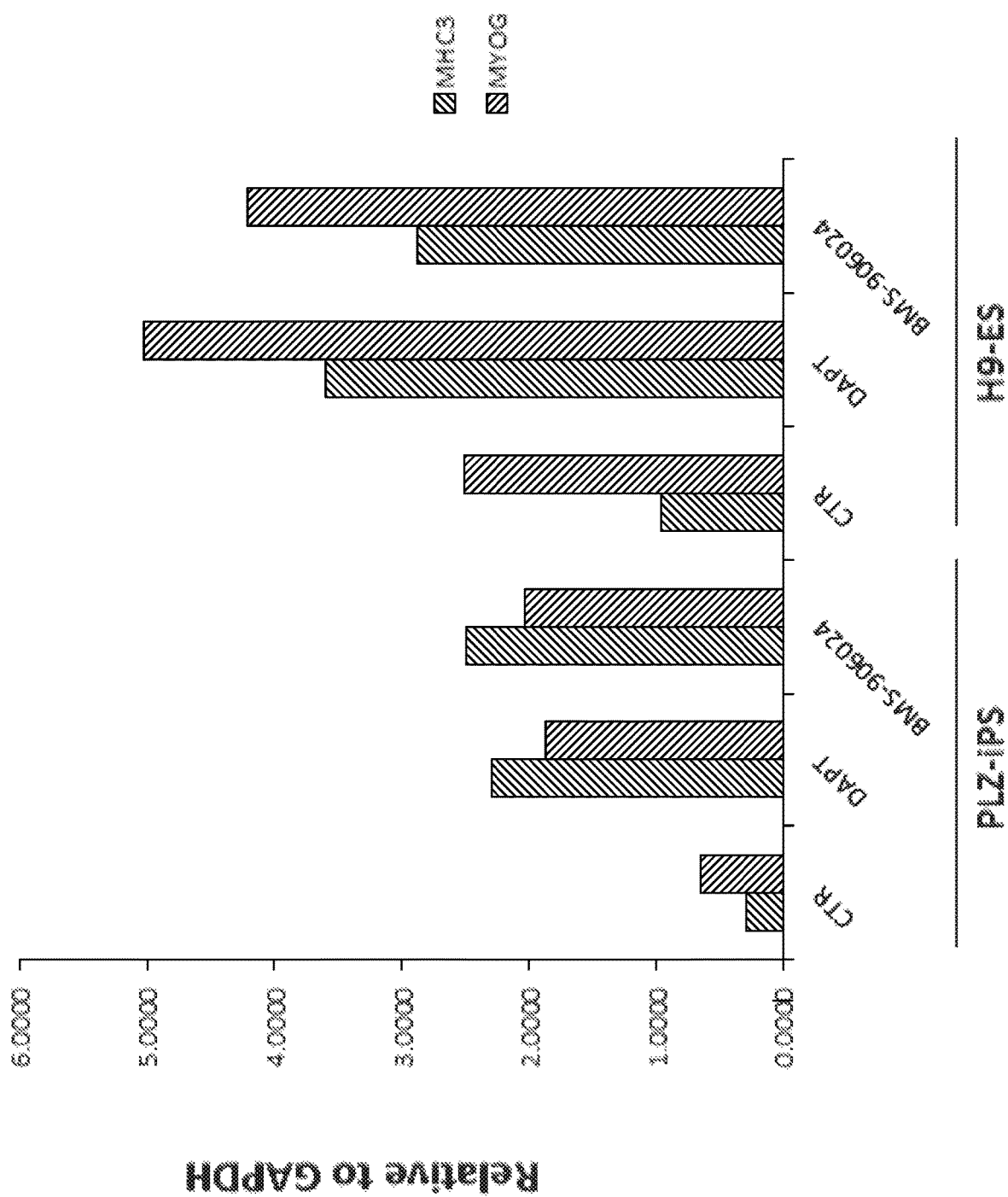
FIG. 1. DAPT and BMS enhance the expression levels of MHC3 and MYOG during differentiation of hES/iPS cell-derived myogenic progenitors using serum-free differentiation medium. Myogenic progenitors derived from hES (H9) and iPS (PLZ) cells were differentiated into myotubes using KOSR based differentiation medium with or without gamma secretase inhibitors DAPT and BMS-906024 at a concentration of 10 µM. RT-qPCR analysis shows that DAPT and BMS-906024 enhance the expression levels of myosin heavy chain 3 (MHC3) and myogenin (MYOG) by 2-3-fold during differentiation when compared to the untreated controls.
Figure 2A:
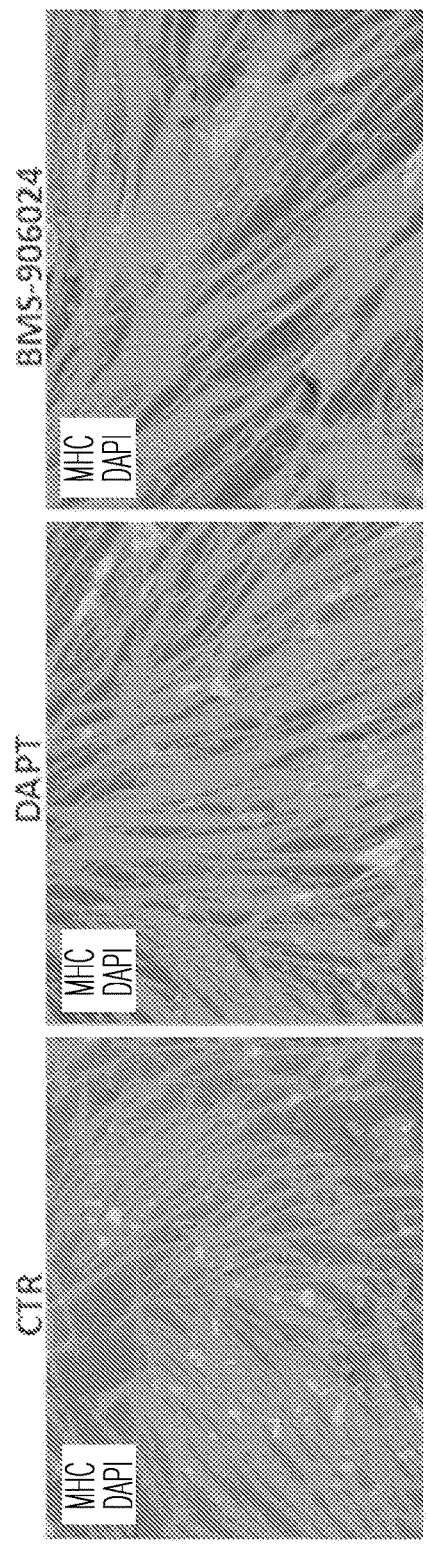
FIGS. 2A-B. DAPT and BMS improve the differentiation of hiPS cell-derived myogenic progenitors using serum free medium. hiPS cell-derived myogenic progenitors were differentiated into myotubes using KOSR-based differentiation medium, with or without gamma secretase inhibitors DAPT and BMS-906024. Immunofluorescence staining for terminal differentiation marker Myosin heavy chain (MHC) (A) shows that DAPT (middle panels) and BMS-906024 (right panels) improve the fusion of the nuclei to give rise to thick myotubes compared to the immature thin myotubes in the untreated control (left panels). Immunofluorescence staining for Myogenin (MYOG) (B) shows that DAPT and BMS-906024 induce clustering of the myogenic nuclei indicating the improved fusion (middle and right panels).
Figure 2B:
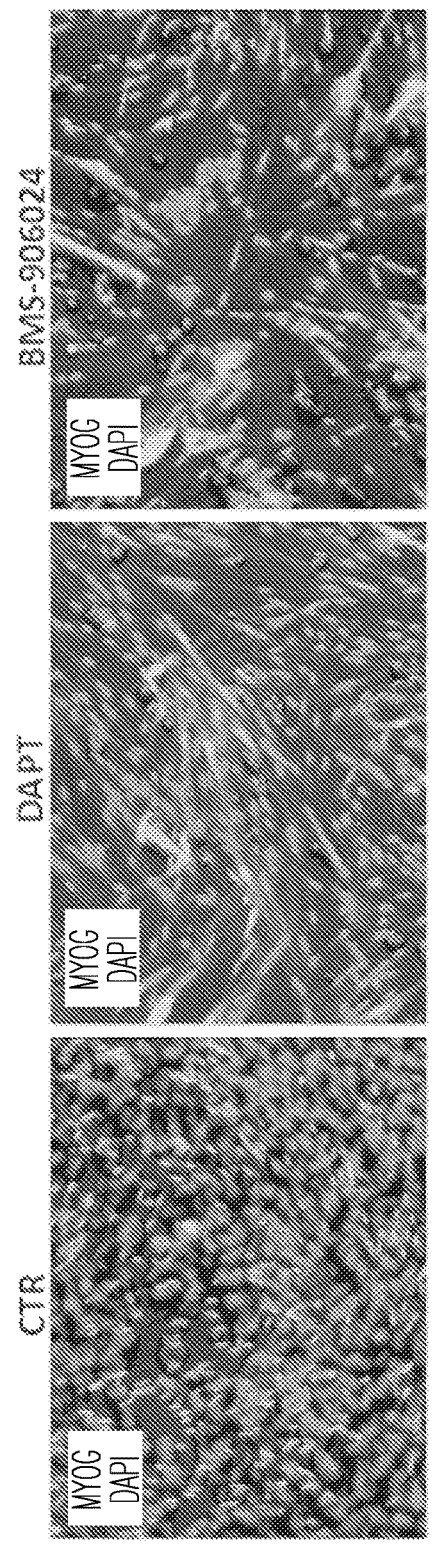
Figure 3A:
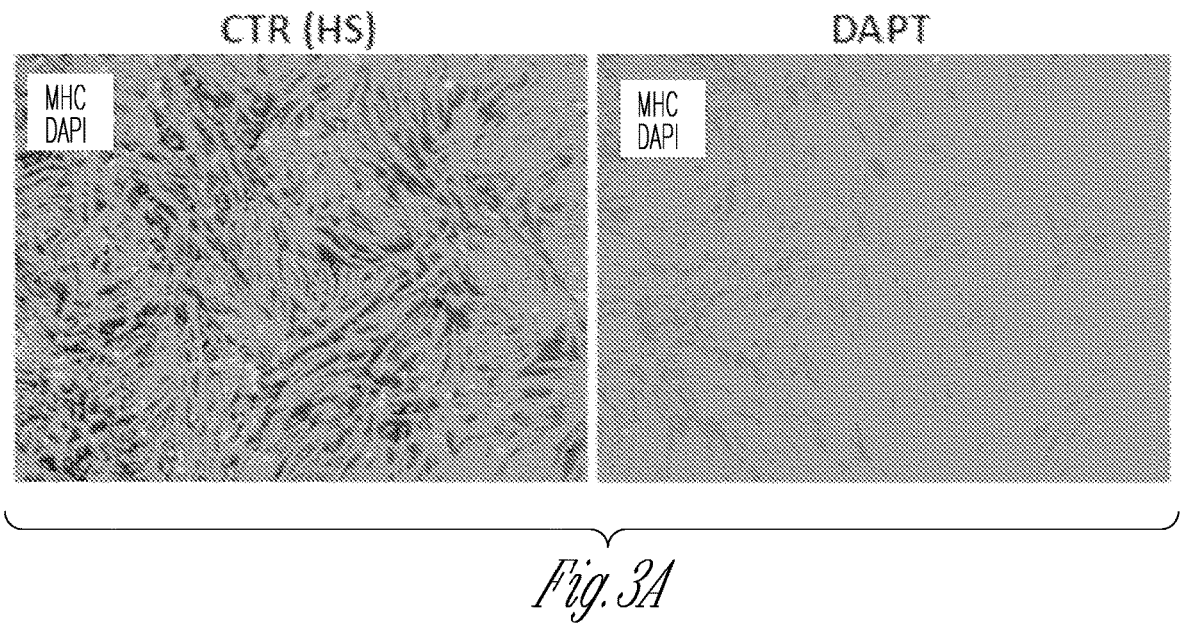
FIGS. 3A-B. DAPT improves the differentiation of hiPS cell-derived myogenic progenitors using horse serum-based medium. hiPS cell-derived myogenic progenitors were differentiated into myotubes using horse serum-based (HS) differentiation medium, with or without gamma secretase inhibitor DAPT. Immunofluorescence staining for terminal differentiation markers Myosin Heavy Chain (MHC) (A) and MYOG (B) shows that DAPT improves the efficiency of the differentiation.
Figure 3B:
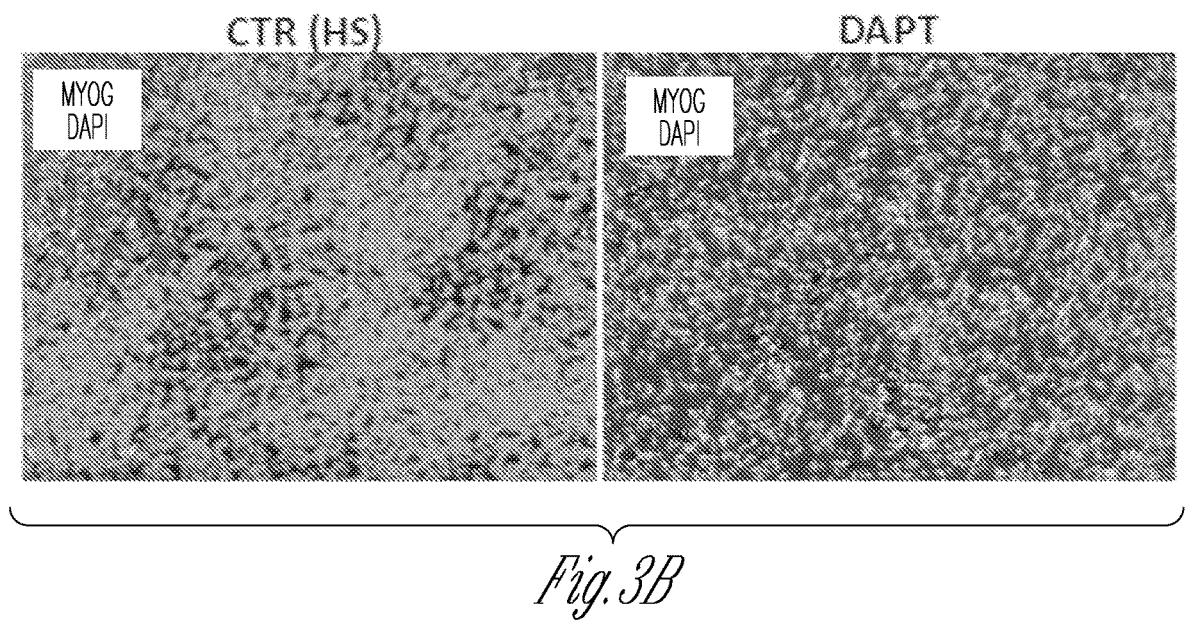
Figure 4A:
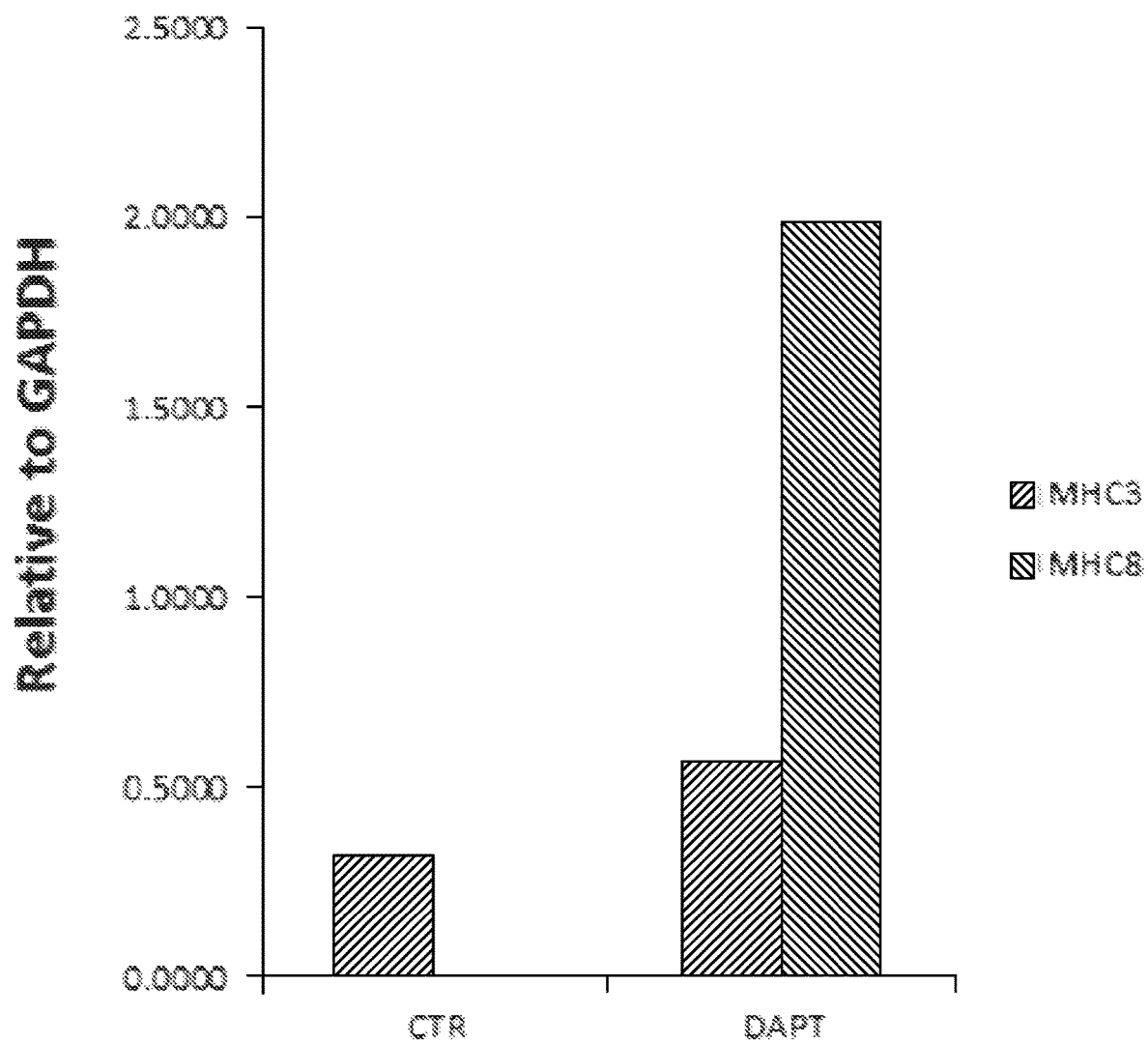
FIGS. 4A-B. DAPT enhances the levels of MHC3, MHC8 and CAPN3 during differentiation of hiPS cell-derived myogenic progenitors using horse serum based medium. hiPS cell-derived myogenic progenitors were differentiated into myotubes using horse serum-based differentiation medium, with or without gamma secretase inhibitor DAPT. RT-qPCR analysis shows that DAPT enhances the expression levels of embryonic myosin heavy chain (MHC3) and neonatal myosin heavy chain (MHC8) (A) during differentiation. The expression level of MHC8 is increased by more than 200-fold during differentiation in the presence of DAPT. DAPT also induces the expression level of CAPN3, which is expressed at very low levels in embryonic muscle but increases upon maturation, (B) by 5-fold when compared to the untreated control.
Figure 4B:
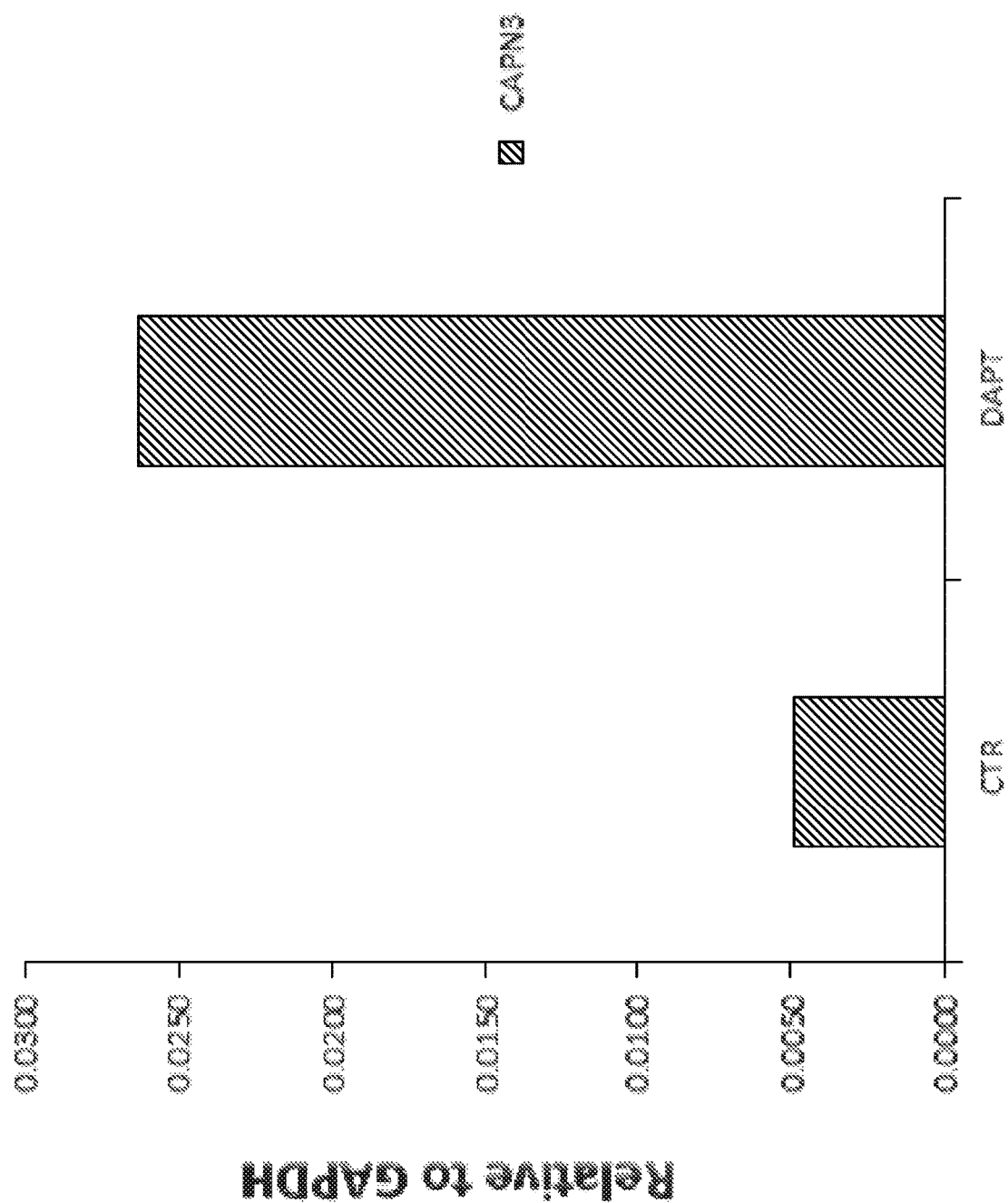

There are several different published protocols for deriving myogenic progenitors from human pluripotent stem cells (Chal and Pourquié, 2017; Barberi, T., et al., 2007); Borchin, B., Chen, J., and Barberi, 2013; Shelton, M., et al., 2014), but most of these protocols give rise to heterogeneous population of cells, which include myotubes but also a high proportion of non-muscle cell types (Kim et al, 2017). If one wishes to generate a purer population of cells, a conditional expression of the PAX7 transcription factor for differentiation of the human pluripotent stem cells into myogenic progenitors to obtain cells that are predominantly homogeneous in myogenic fate can be used. This invention is based on the discovery that efficiency of the differentiation of these myogenic progenitors into myotubes and their subsequent maturation is improved by adding gamma secretase inhibitors to the culture medium.

Such cells/methods find use in disease modeling and drug screening for various skeletal muscle diseases using patient-specific pluripotent stem cells. The cells themselves are also available for treatment purposes and they can be used for the discovery/screening of novel drugs for treatment.

Herein is provided the novel application of gamma secretase inhibitors to improve the in vitro differentiation of iPS cell-derived skeletal muscle progenitors into myotubes, as well as to improve the maturation of myotubes generated in vitro. The gamma secretase inhibitors DAPT and BMS-906024 are identified herein as efficient chemical compounds for this purpose. Other compounds, which are gamma secretase inhibitors, can have a similar effect, such as tripeptide (Z-Leu-Leu-Nle-CHO); LY-685458; YO-01027; Compound E; RO-4929097; MRK-003; MK-0752; and/or PF-03084014. These compounds could also be used to induce maturation of pluripotent stem cell-derived myogenic cells obtained using the method described herein (PAX7 induction), as well as various other muscle differentiation protocols. Other molecules that increase myotube differentiation include, but are not limited to, SB 431542 (S), dexamethasone (De), PD 0325901 (P) and forskolin (F).

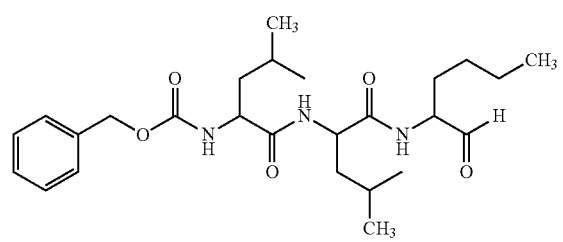

Tripeptide (Z-Leu-Leu-Nle-CHO

LY-685458

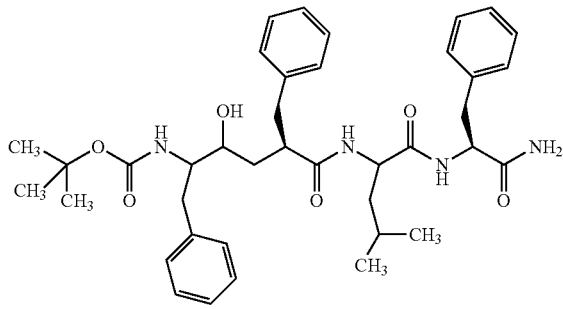

YO-01027

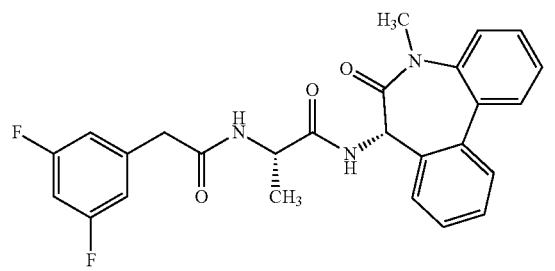

Compound E

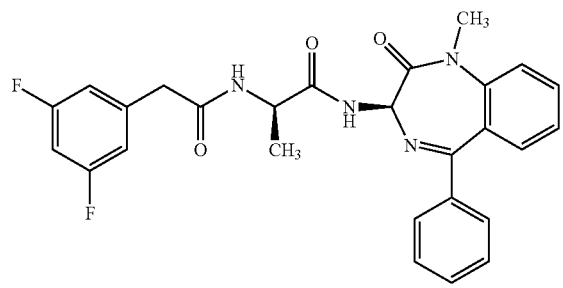

RO-492097

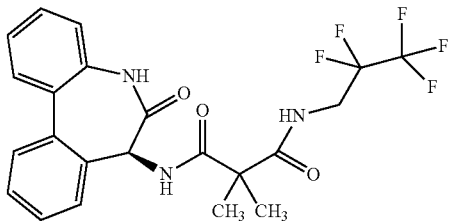

MRK-003

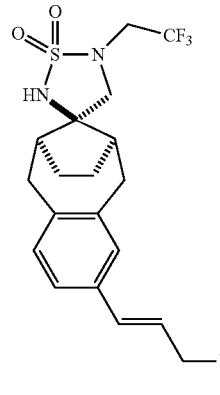

MK-0752

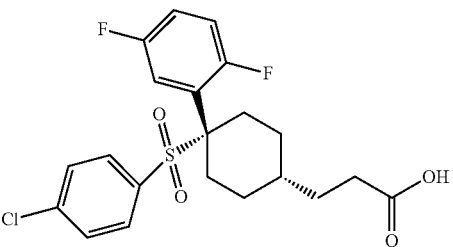

PF-03084014

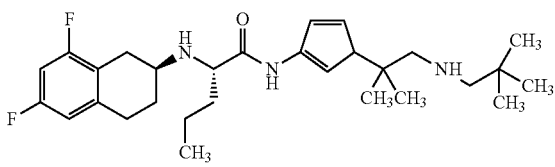

SB 431542

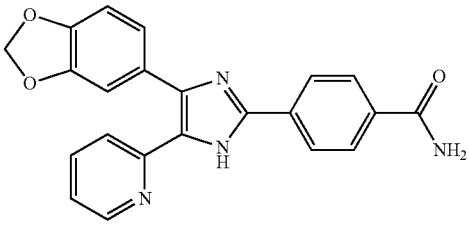

PD 0325901

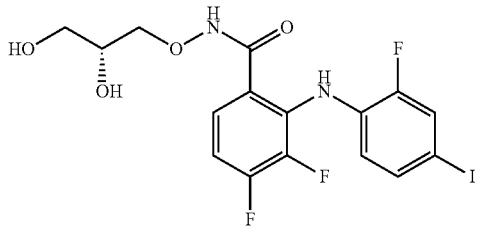

Definitions:

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

"Progenitor cells" are cells produced during differentiation of a stem cell that have some, but not all, of the characteristics of their terminally differentiated progeny. Defined progenitor cells, such as "myogenic progenitor cells," are committed to a lineage, but not to a specific or terminally differentiated cell type.

"Self-renewal" refers to the ability to produce replicate daughter stem cells having differentiation potential that is identical to those from which they arose. A similar term used in this context is "proliferation."

"Expansion" refers to the propagation of a cell or cells without differentiation.

"Cytokines" refer to cellular factors that induce or enhance cellular movement, such as homing of stem cells, progenitor cells or differentiated cells. Cytokines may also stimulate such cells to divide.

"Differentiation factors" refer to cellular factors, preferably growth factors or factors that induce lineage commitment.

The terms "comprises," "comprising," and the like can have the meaning ascribed to them in U.S. Patent Law and can mean "includes," "including" and the like. As used herein, "including" or "includes" or the like means including, without limitation.

Aspects of the Invention

The present invention relates generally to the field of stem cell biology, more specifically the directed differentiation of stem cells, such as human pluripotent stem cells (hPSCs) or multipotent stem cells, including embryonic stem cells (ESC), somatic (e.g., adult) stem cells, and induced pluripotent stem cells (iPSC) using novel culture conditions. Specifically, compositions and methods of the invention are directed to the enhanced formation of myotubes in vitro from stem cells.

Stem Cells

The method functions across a broad range of undifferentiated stem cell lines and is simple to execute. The stem cells for use in the compositions, methods and kits provided herein can be any vertebrate stem cell, including human.

The stem cells include, but are not limited to, embryonic stem cells (including human embryonic stem cells (hESC)), somatic stem cells (e.g., human), and induced pluripotent stem cells (iPSC (e.g., human)).

Embryonic stem cells are pluripotent stem cells derived from the inner cell mass of a blastocyst, an early-stage preimplantation embryo. Human embryos reach the blastocyst stage 4-5 days post fertilization, at which time they consist of 50-150 cells.

Somatic stem cells include adult stem cells which are undifferentiated cells, found throughout the body after development that multiply by cell division to replenish dying cells and regenerate damaged tissues.

Induced pluripotent stem cells (also known as iPS cells or iPSCs) are a type of pluripotent stem cell that can be generated directly from adult cells. iPSCs are typically derived by introducing products of specific sets of pluripotency-associated genes, or "reprogramming factors", into a given cell type. The original set of reprogramming factors are the transcription factors Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers (nanog, LIN28, Glis1).

Stem cells, and those cells differentiated therefrom, can be expanded and further differentiated and/or frozen by way of media and cell culturing methods available to an art worker.

Differentiation/Generation of Pluripotent Stem Cell-Derived Myogenic Cells

Myogenic cells can be obtained by differentiating stem cells by methods available to an art worker. Such methods include those described in Chal and Pourquié (2017), as well the method described herein using PAX7 induction (a conditional expression of the PAX7 transcription factor for differentiation of the human pluripotent stem cells into myogenic progenitors to obtain cells that are predominantly homogeneous in myogenic fate).

The efficiency of the differentiation of these myogenic progenitors into myotubes and their subsequent maturation is improved by adding gamma secretase inhibitors to the culture medium.

Gamma Secretase Inhibitors

Inhibitors of gamma secretase for use in the methods, compositions and kits of the invention include, but are not limited to, DAPT ((2S)—N-[(3,5-Difluorophenyl)acetyl]-L-alanyl-2-phenyl)glycine 1,1-dimethylethyl ester) and BMS-906024 (Dovey et al, 2001; Gavai et al, 2015)

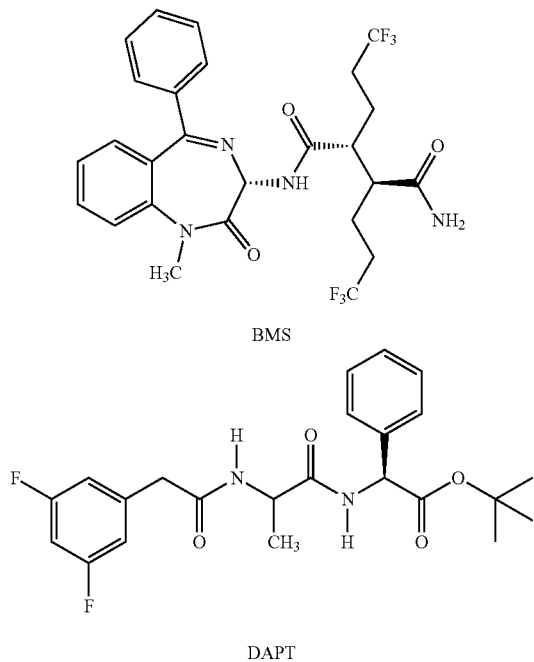

BMS

DAPT

Other molecules that increase myotube differentiation and/or maturation include, but are not limited to, SB 431542 (S), dexamethasone (De), PD 0325901 (P) and forskolin (F).

Differentiated Cell Types

In one embodiment, said the stem cells are differentiated to myogenic progenitors, followed by formation of myotubes exhibiting fetal markers (more so than embryonic markers), such as increased expression of MHC8. In one embodiment, differentiation into myotubes is enhanced, increasing efficiency from about 60% to at least about 90%.

In one embodiment, following the differentiation methods disclosed herein, the differentiated cell is at least 10% up to 100% of said population of cultured cells. Those skilled in the art can readily determine the percentage of myogenic progenitor cells and/or myotubes in a population using various well-known methods, such as fluorescence activated cell sorting (FACS). Ranges in populations comprising myogenic progenitor cells and/or myotubes include about 50-55%, 55-60%, and 65-70%, including about 70-75%, 75-80%, 80-85%; and about 85-90%, 90-95%, and 95-100% of myogenic progenitor cells and/or myotubes produced by the methods described herein. However, populations with lower purity can also be useful, such as about 10-25%, 25-30%, 30-35%, 35-40%, 40-45% and 45-50%. The concentration of myogenic progenitor cells and/or myotubes can be determined according to the gene expression profile within a population.

Genetically-Modified Stem Cells

Stem cells can be genetically altered so as to express, for example, an inducible PAX7 gene. Stem cells can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer. Stem cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Cell Growth

During and differentiation the cells of the invention can be cultured in culture medium that is well established in the art and commercially available from the American Type Culture Collection (ATCC). Such media include, but are not limited to. Dulbecco's Modified Eagle's Medium (DMEM), DMEM F12 medium, Eagle's Minimum Essential Medium, F-12K medium, Iscove's Modified Dulbecco's Medium, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. It is understood that sera can be heat-inactivated at 55-65° C. if deemed necessary to inactivate components of the complement cascade. Modulation of serum concentrations, or withdrawal of serum from the culture medium can also be used to promote survival of one or more desired cell types. In one embodiment, the endodermal progenitor cells are cultured in the presence of FBS/or serum specific for the species cell type. For example, stem cells can be isolated and/or expanded with total serum (e.g., FBS) concentrations of about 0.5% to about 5% or greater including about 5% to about 15%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution (HBSS), Earle's Salt Solution, antioxidant supplements, MCDB-201 supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Also contemplated is the use of feeder cell layers. Feeder cells are used to support the growth of fastidious cultured cells. Feeder cells are normal cells that have been inactivated by γ-irradiation. In culture, the feeder layer serves as a basal layer for other cells and supplies cellular factors without further growth or division of their own (Lim and Bodnar 2002). Examples of feeder layer cells typically used with liver cell cultures are hepatocytes and embryonic fibroblasts (Suzuki, A. et al. 2000), but can be any post-mitotic cell that is capable of supplying cellular components and factors that are advantageous in allowing optimal growth, viability, and expansion of endodermal progenitor cells. In some cases, feeder cell layers are not needed to keep cells in an undifferentiated, proliferative state, as leukemia inhibitory factor (LIF) has anti-differentiation properties. Often, supplementation of a defined concentration of LIF is all that is necessary to maintain cells in an undifferentiated state.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel®, thrombospondin, and/or vitronectin.

The maintenance conditions of cells can also contain cellular factors that allow cells to remain in an undifferentiated form. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors. In fact, these factors may elicit unwanted effects, depending on the cell type.

Myogenic progenitor cells can be selected based on the markers (gene and/or protein) described herein. Accordingly, positive selection methods can be used, either alone or together with the methods described above, to identify and/or isolate the cells of the invention. Methods of positive selection can include visual selection, using microscopy and/or other means of detection, including, but not limited to, immunoblotting, immunofluorescence, and/or enzyme-linked immunosorbent assay. Other methods of positive selection can also include, but are not limited to, additional selective culture techniques (e.g., variable cell densities or amounts of $CO_2$), flow cytometry, RT-PCR, and/or microchip-based methods of cell separation.

The following examples are intended to further illustrate certain embodiments of the invention and will not limit the scope of the invention in any way.

EXAMPLES

Example I
Introduction

A protocol for derivation of skeletal muscle progenitors from human pluripotent stem cells which give rise to myotubes both in vitro and in vivo has been developed. In vitro-generated myotubes remain immature, resembling the embryonic state. Described herein are chemical compounds that through inhibition of the gamma secretase protein, are able to improve the efficiency of differentiation and maturation of myotubes generated from iPS-derived skeletal muscle progenitors.

Materials and Methods
Cell Culture and Differentiation Procedure

Human induced Pluripotent Stem Cells (hiPSC, PLZ) or Embryonic Stem Cells (hESC, H9) were transduced with the lentiviral constructs pSAM2-PAX7-ires-GFP and pFUGW-rtTA to generate doxycycline-inducible PAX7 (iPAX7) PS-cells as previously reported (Darabi, 2012). iPAX7-PS cells were cultured on matrigel-coated flasks using mTeSR1 medium (Stem Cell Technology). Cells were differentiated to myogenic progenitors as previously described (Darabi and Perlingeiro, 2016). Briefly, iPAX7-PS cells were detached with Accumax and $1\times10^6$ cells were plated in 6 cm non-adherent Petri dishes with mTeSR1 supplemented with 10 uM Y-27632 (ROCK inhibitor) and incubated at 37° C., 5% $CO_2$ on a shaker at 60 RPM for 48 h. Then, medium was replaced with EB Myogenic (EBM) Medium supplemented with 10 uM CHIR990217 (GSK3-β inhibitor) and 10 uM Y-27632. Three days later supplements were removed by changing to fresh medium. At day 7, EBs were plated on gelatin-coated flasks with EBM medium+10 ng/ml human basic FGF (bFGF) and three days later 1 ug/ml of doxycycline was added to the medium to induce PAX7 expression. Cells were harvested by trypsinization at day 14 and subsequently FACS sorted for GFP(+) expression. From this point, cells are considered as myogenic progenitors and cultured on gelatin-coated flasks using EBM medium+10 ng/ml bFGF+1 ug/ml Dox.

For terminal differentiation, myogenic progenitors at P3-P5 were plated on gelatin-coated dishes with EBM medium+10 ng/ml bFGF+1 ug/ml Dox. Upon reaching 100% confluency, medium was removed and replaced with knockout serum replacement (KOSR) or horse serum based terminal differentiation medium (TDM) supplemented with 10 uM DAPT, 10 uM BMS-906024.5 days after terminal differentiation, cells were fixed or collected for RNA analysis.

Immunofluorescence

After 5 days of terminal differentiation, cells were washed with PBS and fixed with 4% PFA/PBS for 10 min. Then, cells were permeabilized with 0.3% Triton X-100/PBS for 15 min and blocked with 3% BSA/PBS for 20 min. Cells were incubated with a primary antibody that recognizes all MHC isoforms (MF-20, Developmental Studies Hybridoma Bank) overnight at 4° C. The next day, cells were incubated with an Alexa-555 secondary antibody supplemented with DAPI for 1 h at RT. Cells were analyzed by epifluorescence microscopy.

Western Blot

Terminally differentiated myotubes were collected with Lysis buffer (RIPA buffer, Sigma) supplemented with a cocktail of protease inhibitors (cOmplete, Roche). 50 ug of protein extracts were loaded in a 10% polyacrylamide gel for subsequent SDS-PAGE following standard procedures. Proteins were transferred from the gel to a PVDF membrane by wet transfer for 1.5 h at 100v. Membranes were blocked with 5% non-fat milk/TBS-T for 1 h at RT prior to their incubation with a primary antibody specific to MHC8 (N3.36, Developmental Studies Hybridoma Bank). After 3×10 min TBS-T washings, membranes were incubated with a Horseradish peroxidase-linked secondary antibody for 1 h at RT. Membranes were washed 3× with TBS-T for 10 min and then incubated with Pierce ECL Western blotting substrate (Thermo Scientific) according to the manufacturer's instructions for the detection of the target proteins. β-tubulin was used as a loading control.

RNA Isolation and qPCR Analysis

Differentiated myotubes (5d) were collected with TRIzol (Thermo Fisher Scientific) and RNA was purified using the Direct-zol RNA MiniPrep Plus (Zymo Research) following manufacturer's instructions. cDNA was obtained by RT-PCR using SuperScript VILO (Invitrogen) and qPCR was performed by using the Premix Ex Taq ROX plus (Takara) and TaMan probes (Thermo Fisher Scientific) specific to the genes of interest. qPCR was done with a QuantStudio 6 Flex Real-Time PCR System (Thermo Fisher Scientific). Data was normalized to GAPDH expression.

Results

Human Pluripotent Stem (PS) cells can be efficiently differentiated into the myogenic lineage through the controlled expression of the transcription factor PAX7. Resulting myogenic progenitors can be terminally differentiated into myotubes in vitro with the purpose of modeling the muscle phenotype of muscle genetic diseases. However, the embryonic nature of human PS cell-derivatives leads to the generation of myotubes with an embryonic or immature profile, as demonstrated by the predominant expression of embryonic Myosin Heavy Chain (MHC3) as well as by the size of the cells (thinner, with fewer nuclei), therefore limiting the potential of these cells in modelling diseases that require further matured myotubes. Gamma secretase inhibitors were identified as compounds that not only enhance the terminal differentiation of human PS cell-derived myogenic progenitors, but also promote additional maturation of generated myotubes, and typically within 5 days of differentiation.

Figure 5:
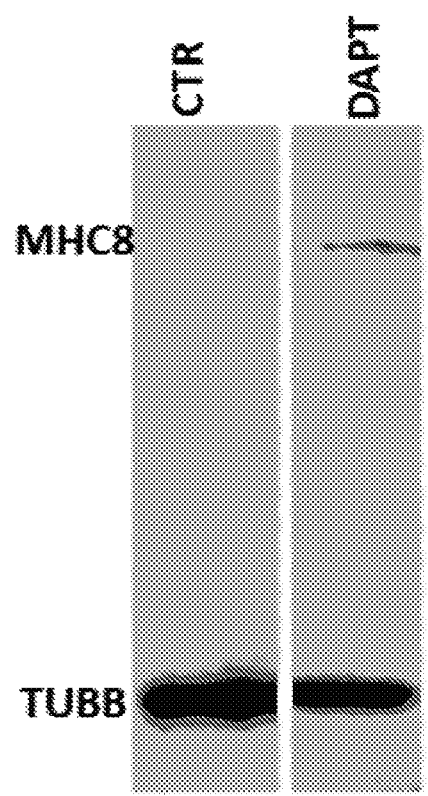
FIG. 5. DAPT induces the expression of MHC8 protein during differentiation of hiPS cell-derived myogenic progenitors. hiPS cell-derived myogenic progenitors were differentiated into myotubes using horse serum-based differentiation medium, with or without gamma secretase inhibitor DAPT. Western blot shows that neonatal Myosin Heavy Chain (MHC8) can be detected only in the presence of DAPT. β-Tubulin (TUBB) was used as the loading control.
Figure 7A:
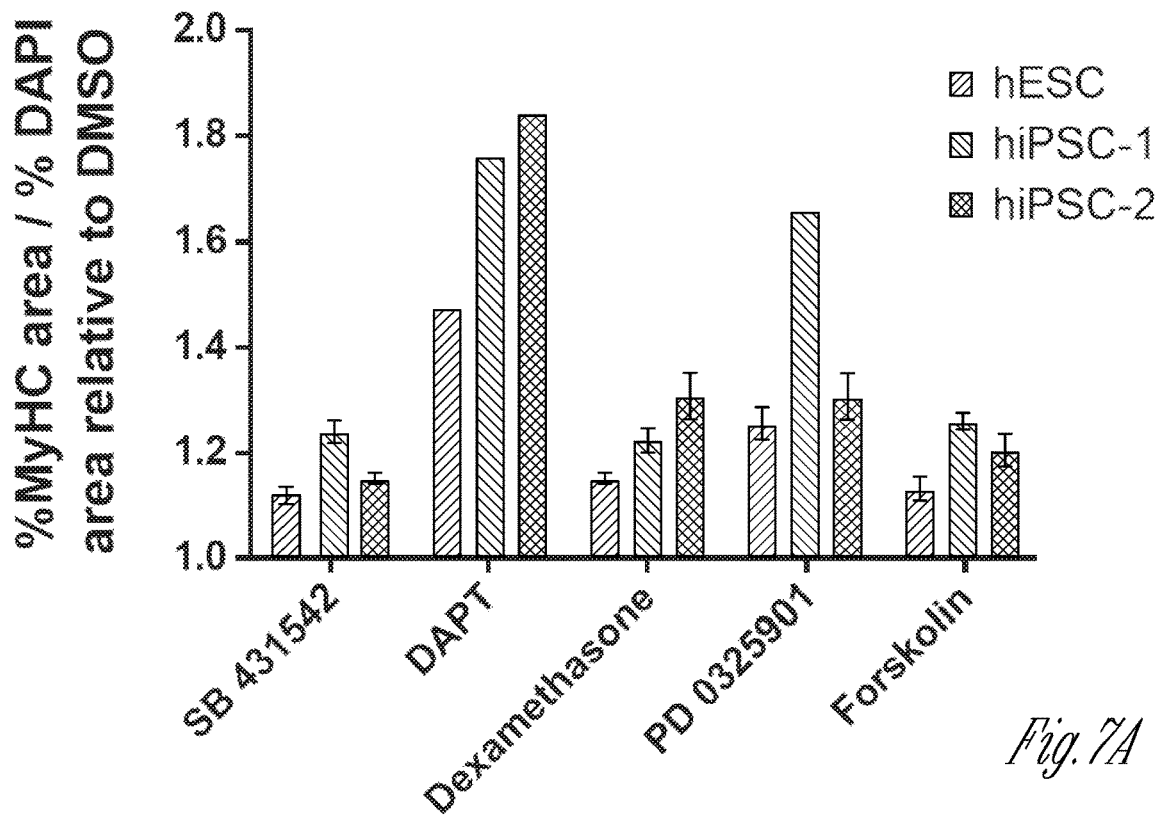
FIGS. 7A-C. Small molecule screening under terminal differentiation conditions of hiPS cell-derived myotubes reveals five candidates that enhance myotube formation and promotes in vitro maturation. (A) Bar graph shows the ratio of MyHC area (%) and DAPI area (%) relative to DMSO of selected small molecule candidates used during terminal differentiation of myotubes derived from three cell lines (hESC-1, hiPSC-1 and hiPSC-2). All five candidates increased significantly the MyHC/DAPI ratio compared to DMSO (p<0.001). Data are shown as mean±SEM. (B) Bar graph shows the ratio of MyHC area (%) and DAPI area (%) relative to DMSO of small molecules used during terminal differentiation of myotubes derived from three cell lines (hESC-1, hiPSC-1 and hiPSC-2). All six small molecules significantly decreased the MyHC/DAPI ratio compared to DMSO (p<0.001), showing detrimental effect on myogenic terminal differentiation. Data are shown as mean±SEM. (C) Myogenin and MyHC profile (MYH2, MYH3, MYH7 and MYH8) expression analysis of myotubes treated with individual candidates from (A) during terminal differentiation. Data are shown as mean±SEM. *p<0.05, p<0.01, *p<0.001
Figure 7B:
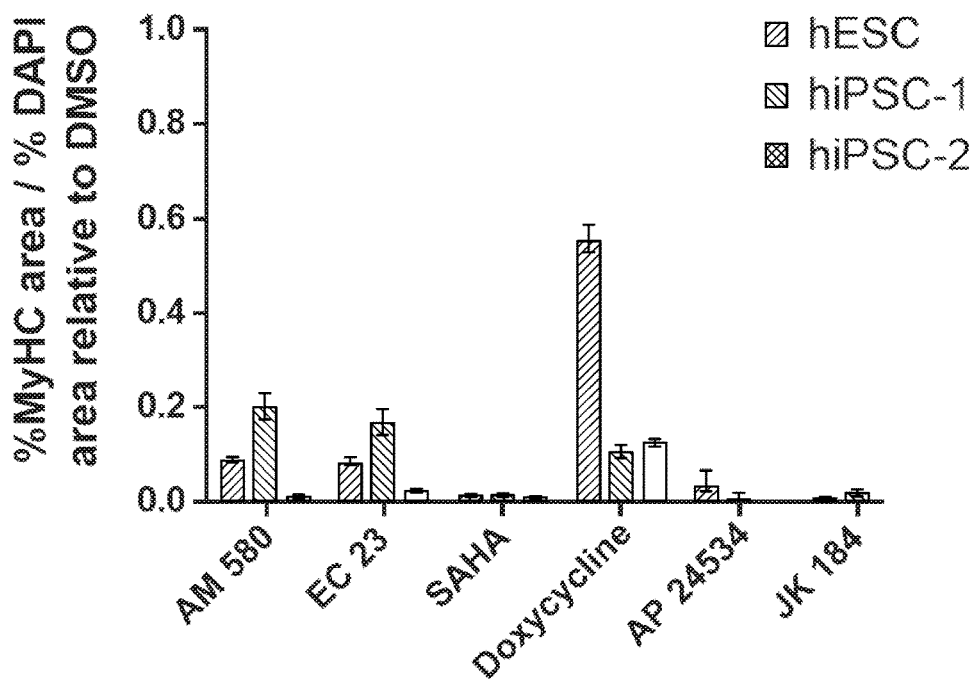
Figures 1, 7C:
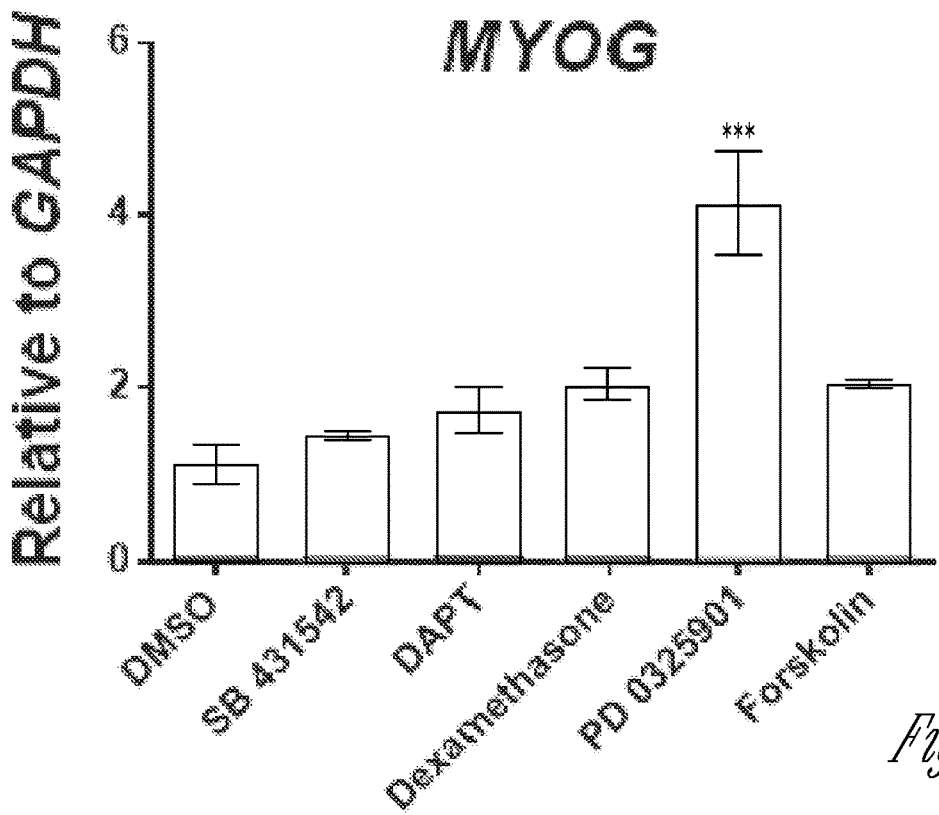
Figures 2, 7C:
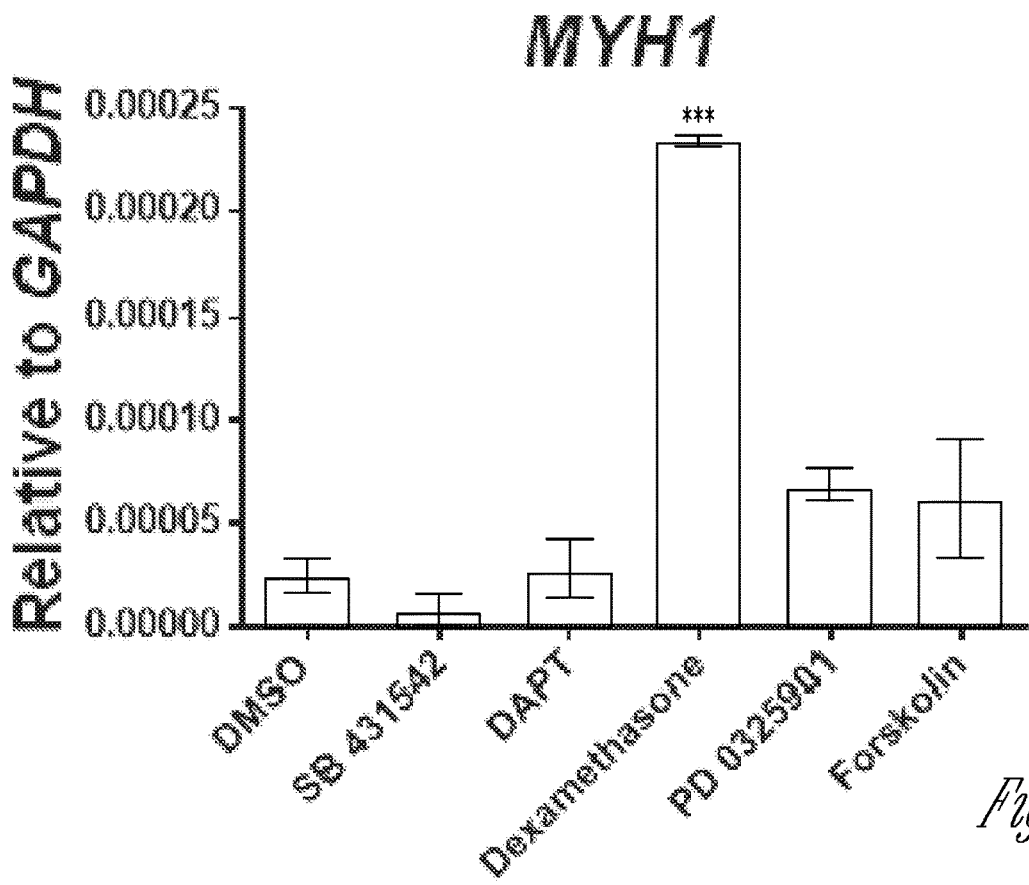
Figures 3, 7C:
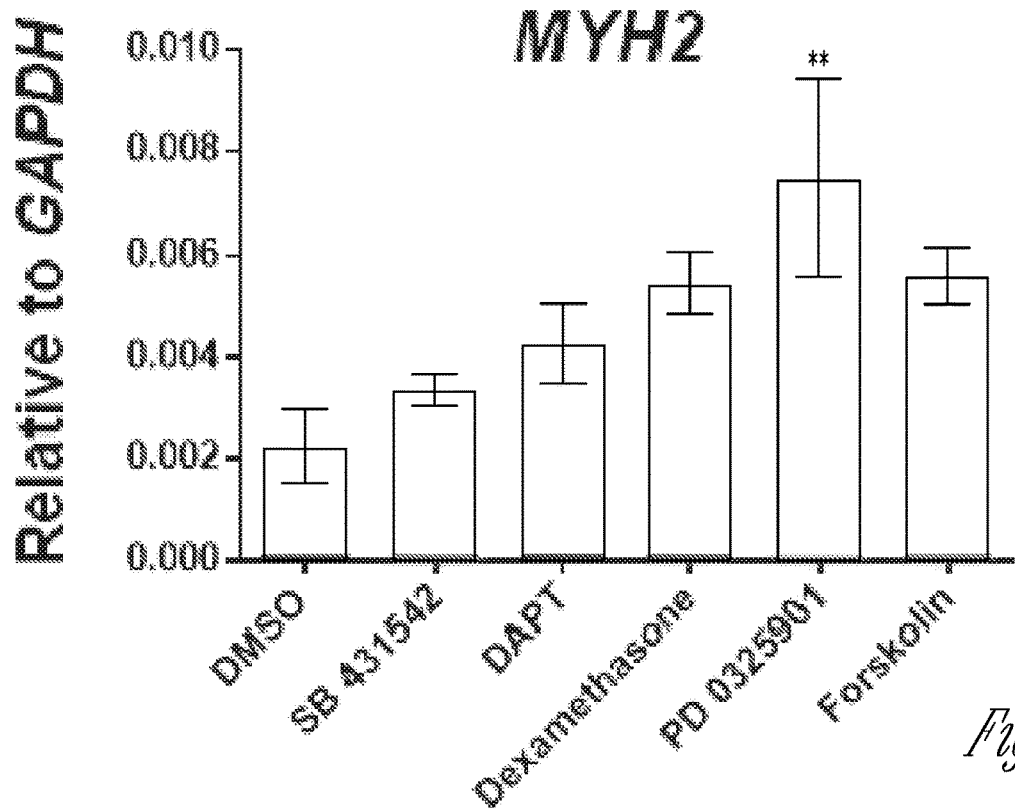

The addition of 10 uM DAPT or 10 uM BMS-906024 to the terminal differentiation medium, which consists of KOSR- or horse serum-based media, results in increased mRNA expression levels of MHC3 and Myogenin following 5 days of incubation at 37° C. (FIG. 1), when compared to non-treated cells. This was confirmed by an increase of MHC(+) myotubes and Myogenin(+) nuclei by immunostaining (FIGS. 2 and 3). Therefore, there is an improvement in the terminal differentiation efficiency. In addition, increased hypertrophy and fusion of resulting myogenic cells was observed (FIG. 2). Under such differentiation conditions, a dramatic increase in the mRNA and protein expression levels of MHC8 was found (FIGS. 4 and 5), which is the MHC isoform predominantly expressed in the fetal and neonatal stages.

Figures 4, 7C:
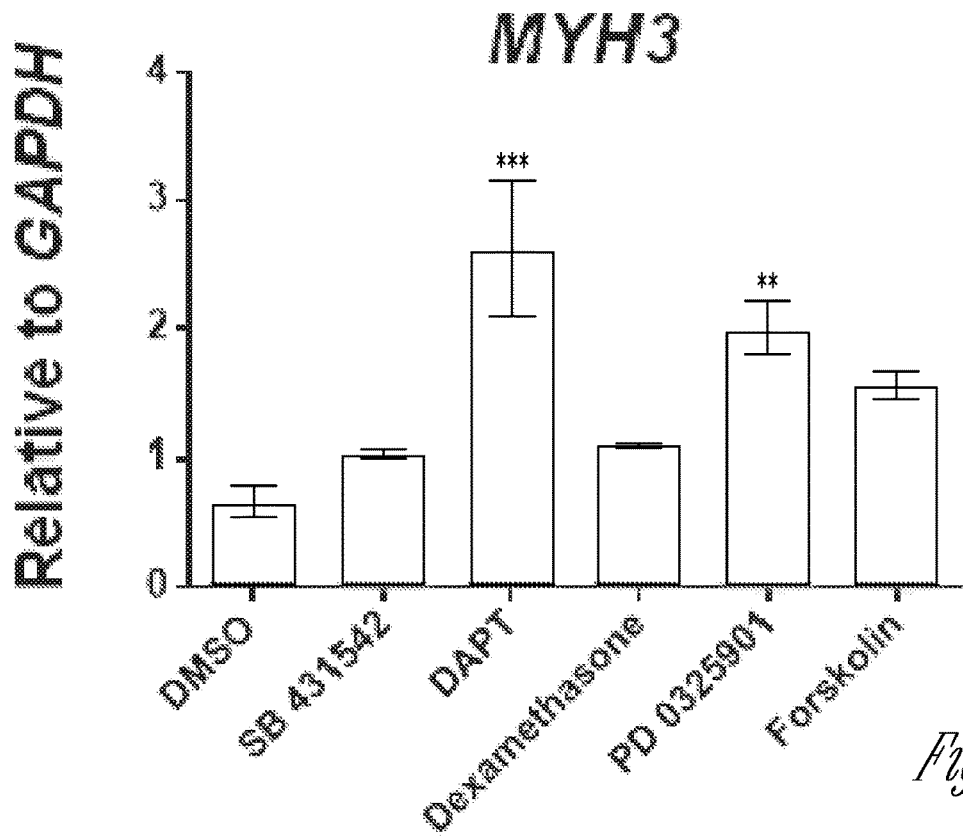
Figures 5, 7C:
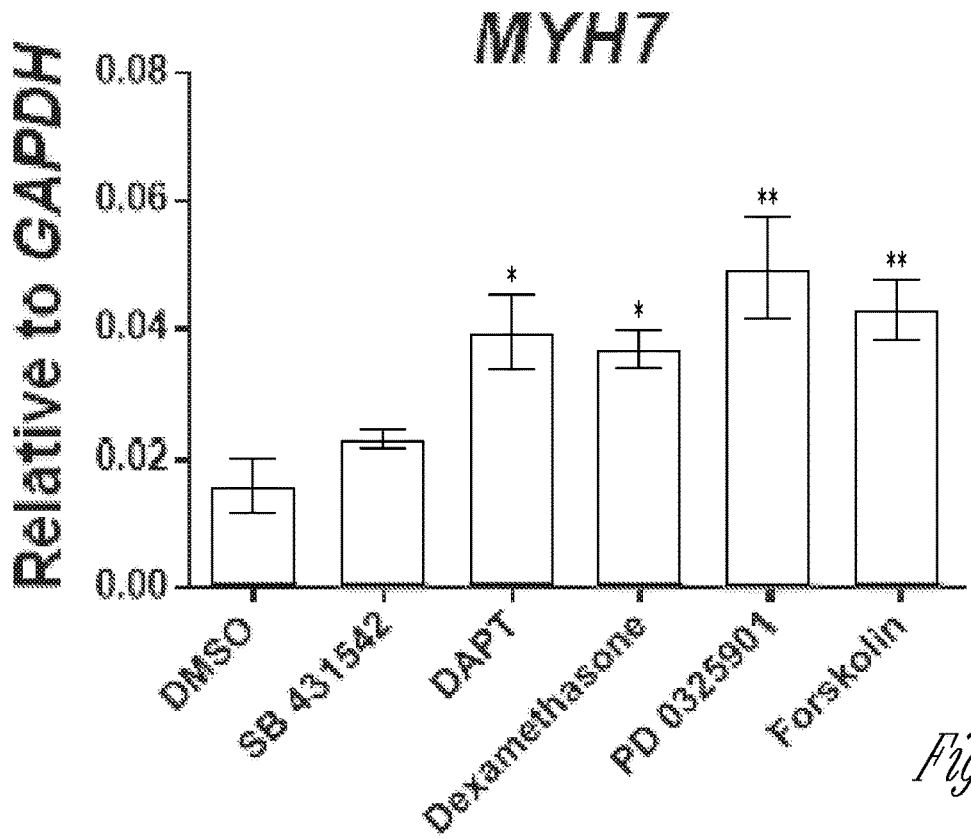

By promoting the in vitro maturation of PS cell-derived myotubes through the gamma secretase inhibitors DAPT and BMS-906024, one can study muscle-specific proteins that are related to muscle diseases but are not expressed in an embryonic or immature state, like Calpain-3, which is relevant for modeling limb girdle muscular dystrophy type 2A (FIG. 4).

Example II

Introduction/Results/Discussion

Figures 6, 7C:
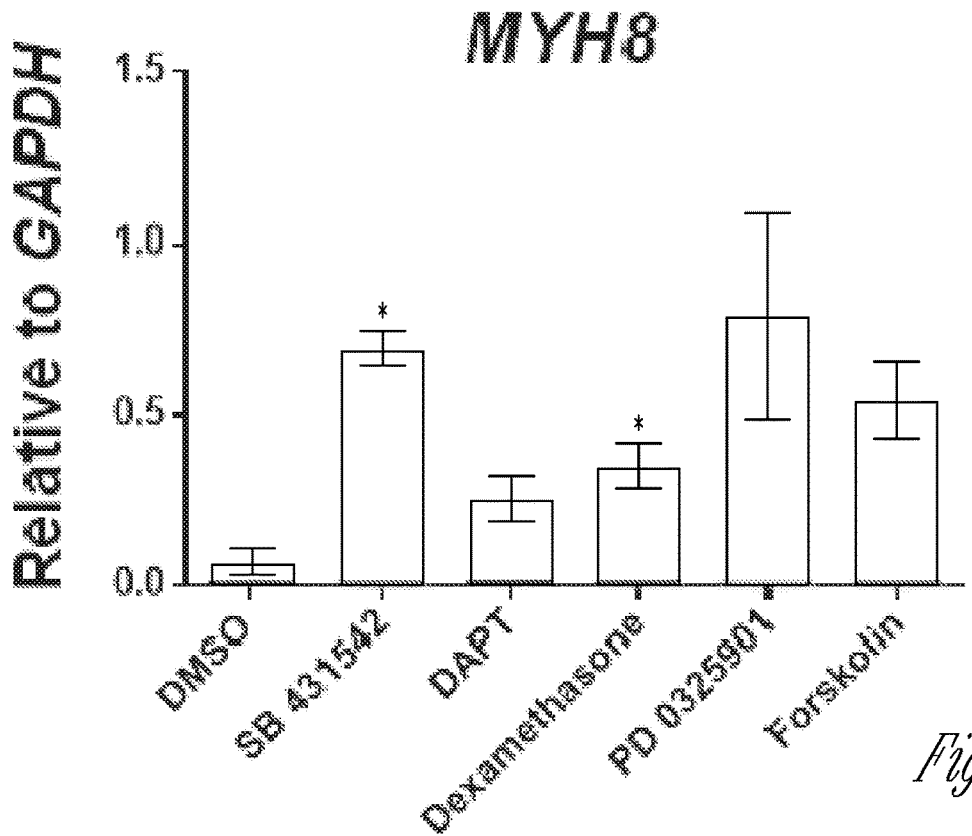
Figure 8A:
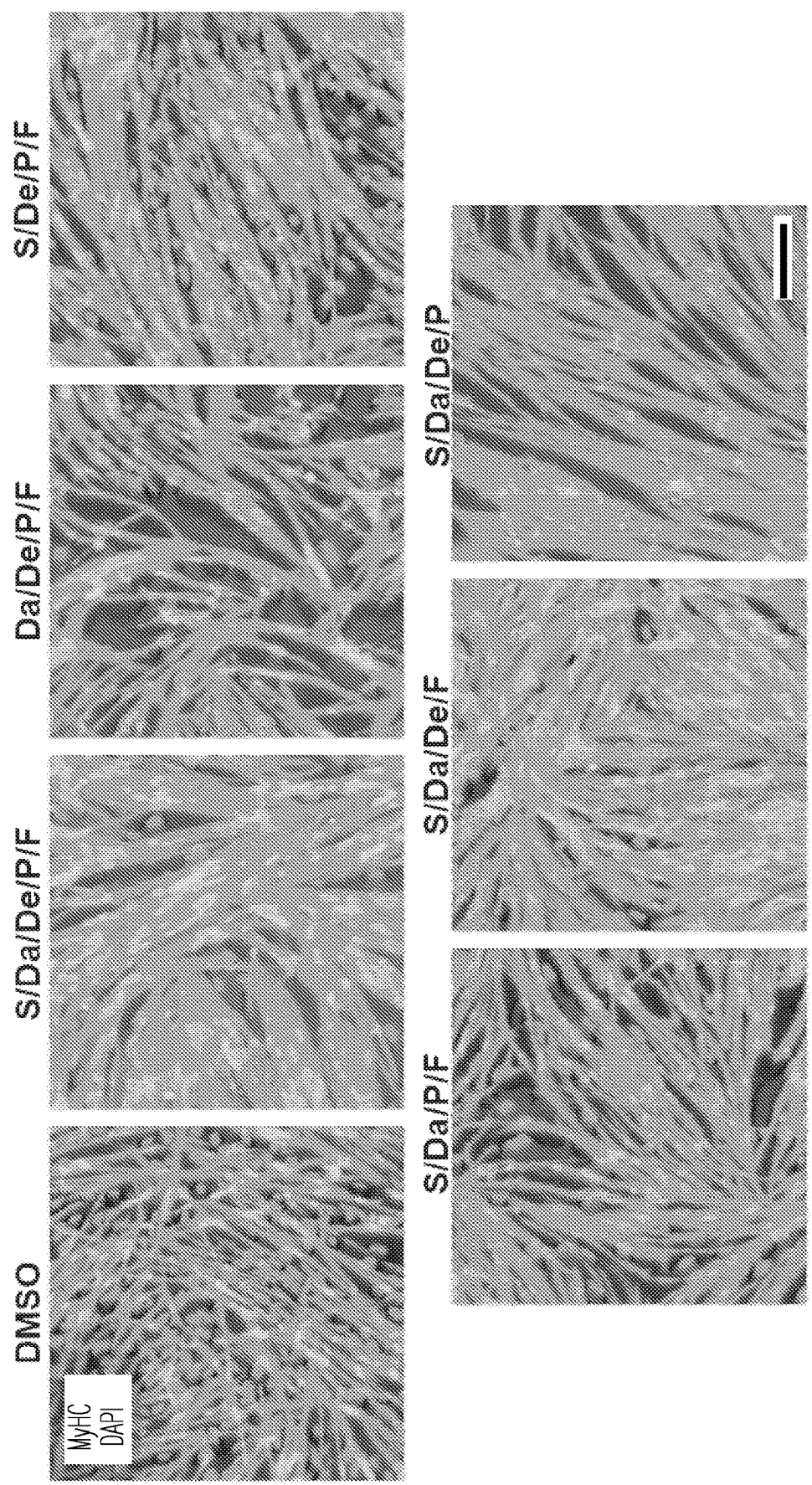
FIGS. 8A-E. Treatment of hiPS cell-derived myotubes under terminal differentiation with combinations of selected small molecules potentiates myotube differentiation, fusion and maturation in vitro. (A) Representative images of immunostaining of myotubes differentiated with combinations of small molecule candidates in the terminal differentiation step. Scale bar is 100 µm. (B) Bar graph shows the ratio of MyHC area (%) and DAPI area (%) relative to DMSO of different combinations of small molecules used during terminal differentiation of myotubes derived from hiPSC-1 cell line. All candidates increased significantly the MyHC/DAPI ratio compared to DMSO (p<0.001). Data are shown as mean±SEM. (C) Bar graph shows the percentage of fusion index of myotubes treated with combinations of small molecules during the terminal differentiation step. ***p<0.001. (D) Distribution bar graph represents the frequency (%) of number of nuclei per myotube upon treatment with combinations of small molecules during the terminal differentiation step. (E) Myogenin and MyHC profile (MYH2, MYH3, MYH7 and MYH8) expression analysis of myotubes treated with combinations of small molecule candidates during terminal differentiation. Data are shown as mean±SEM. *p<0.05, p<0.01, *p<0.001
Figure 8B:
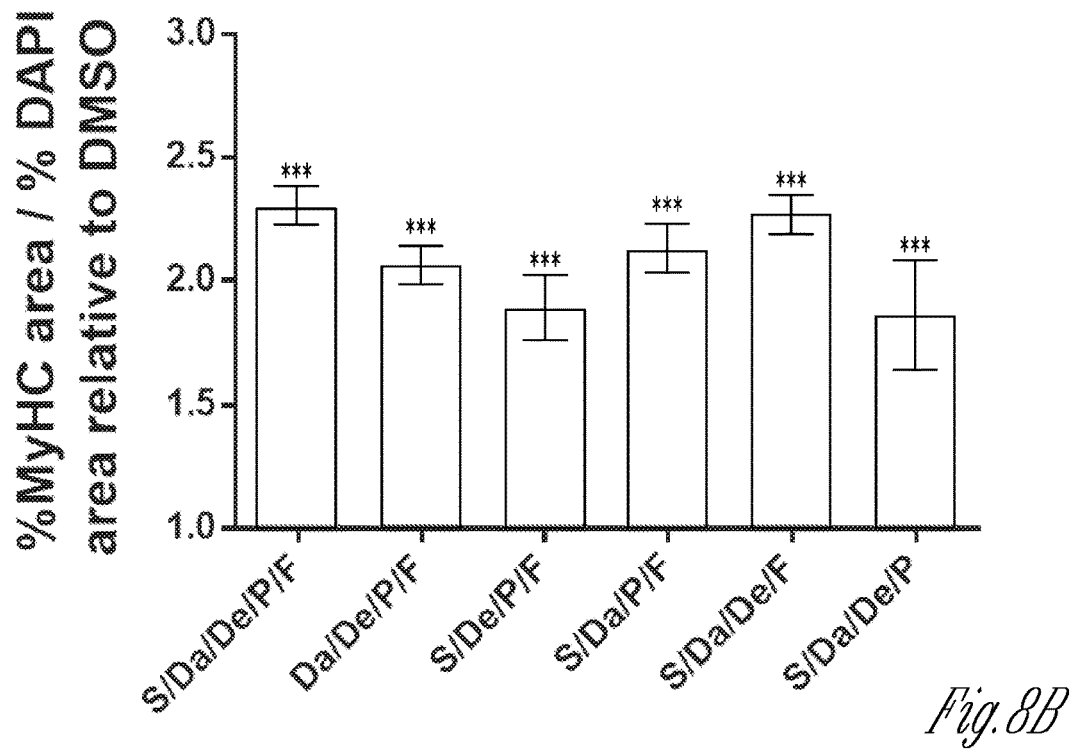
Figure 8C:
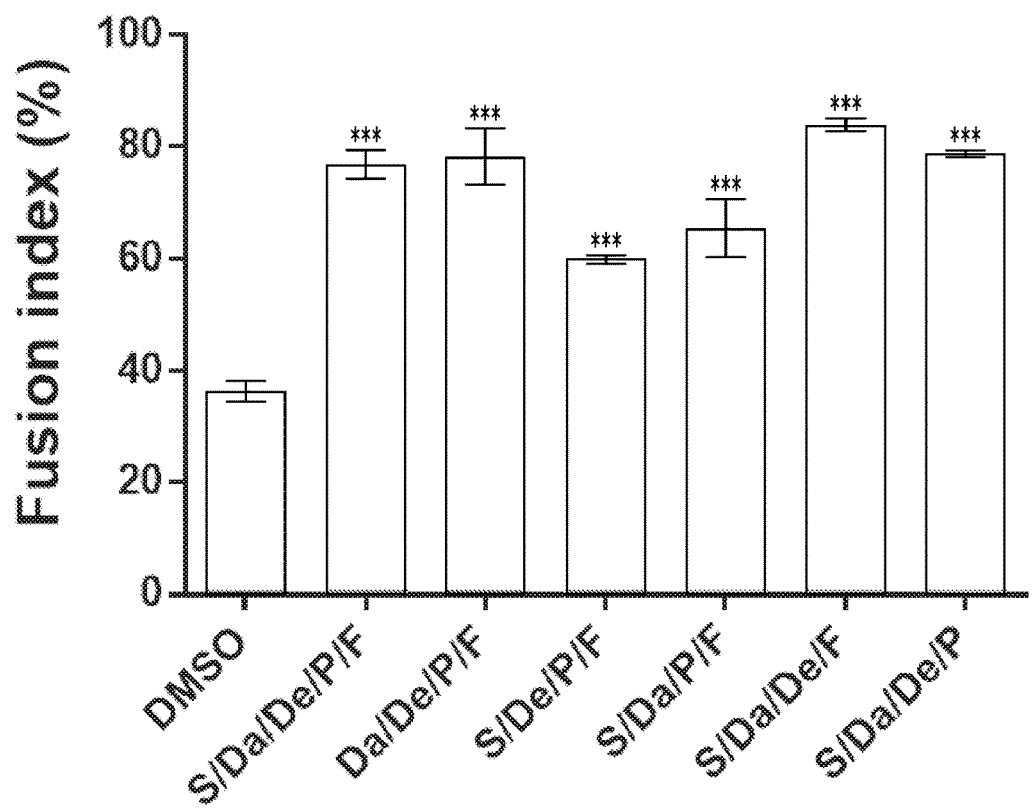
Figure 8D:
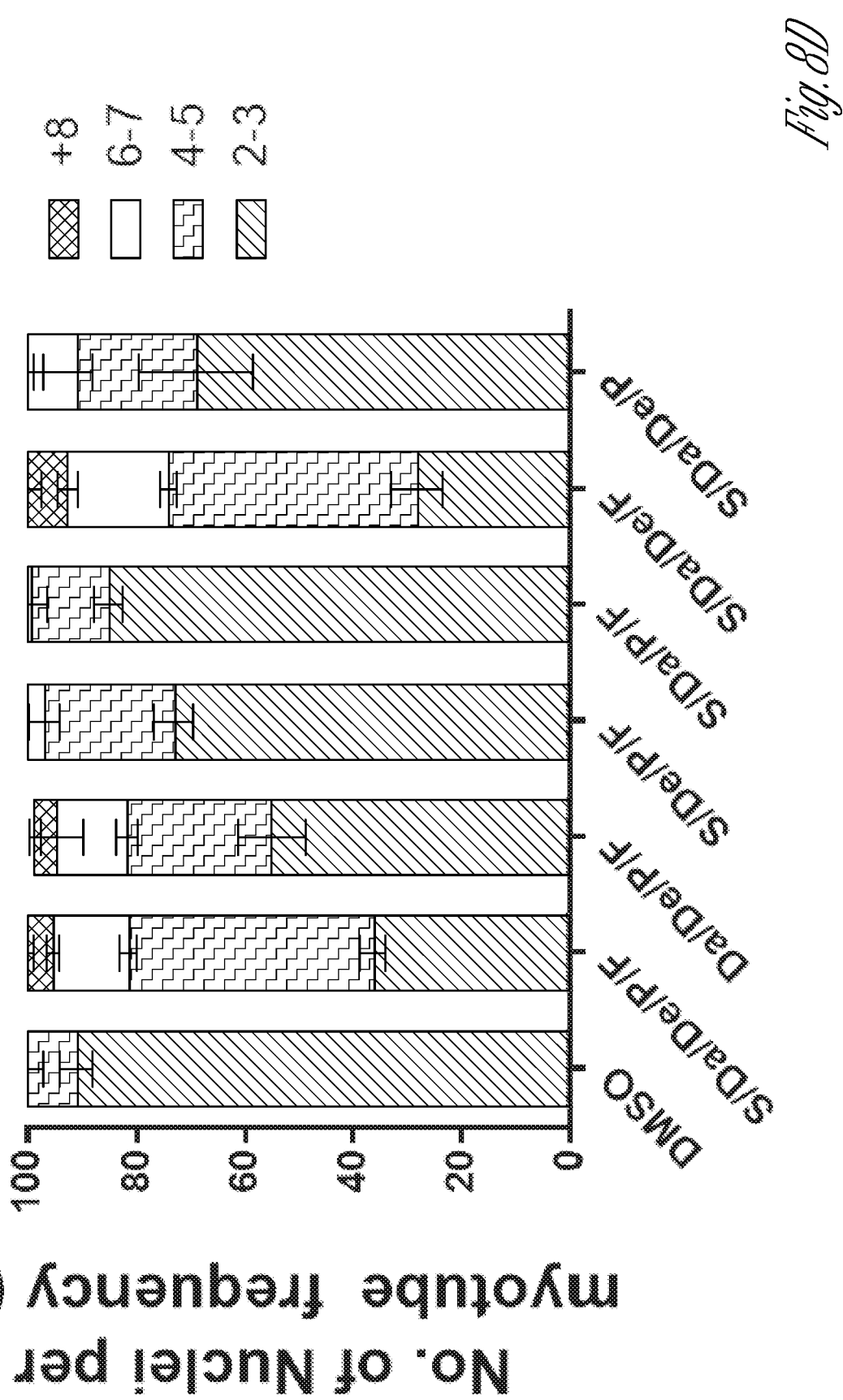
Figures 1, 8E:
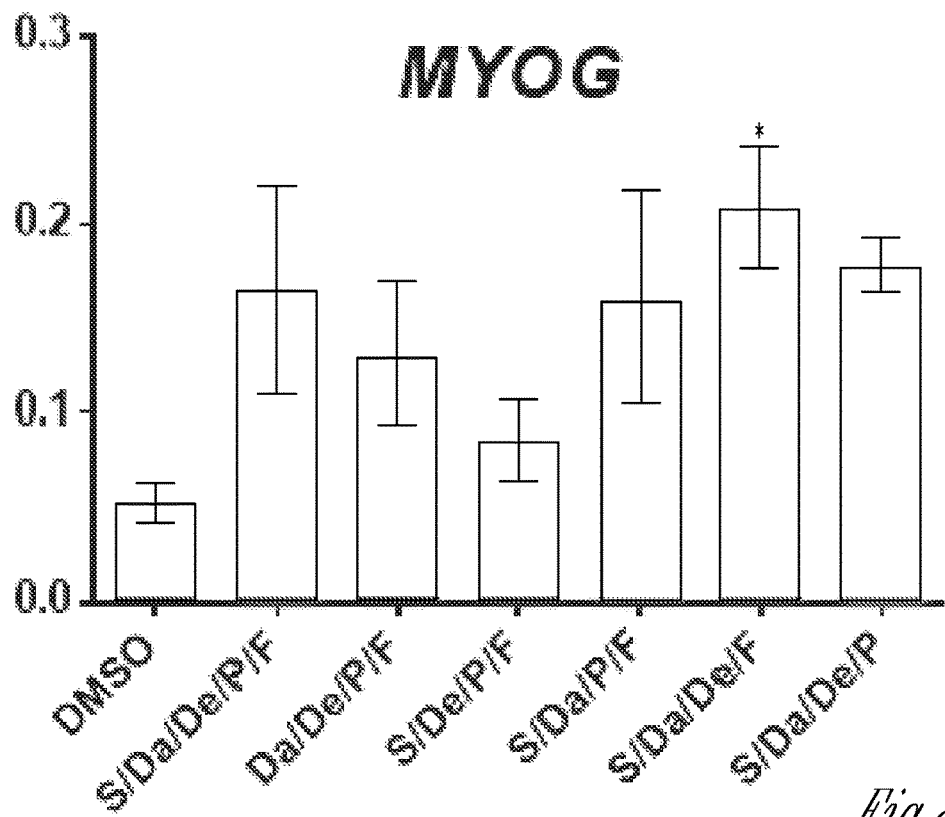
Figures 2, 8E:
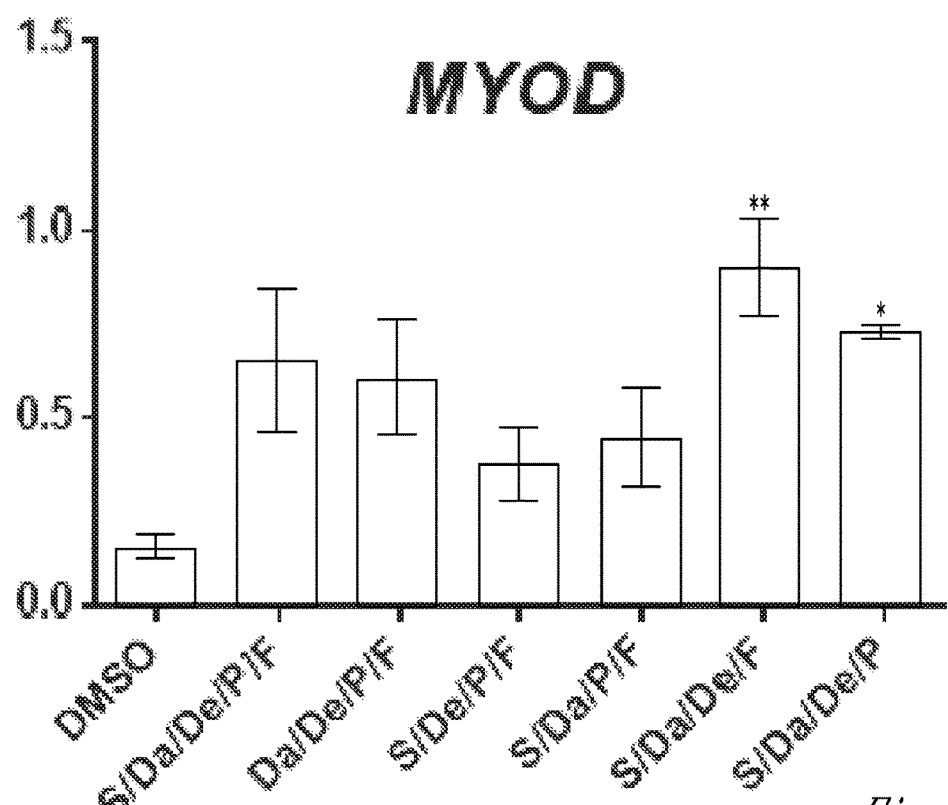
Figures 3, 8E:
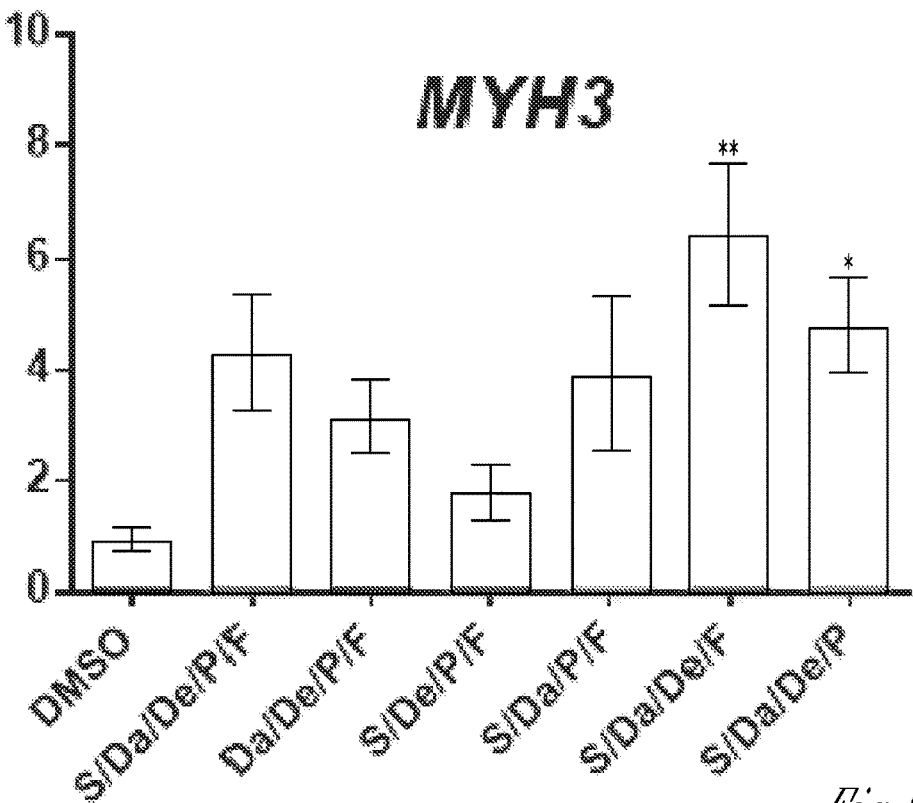
Figures 4, 8E:
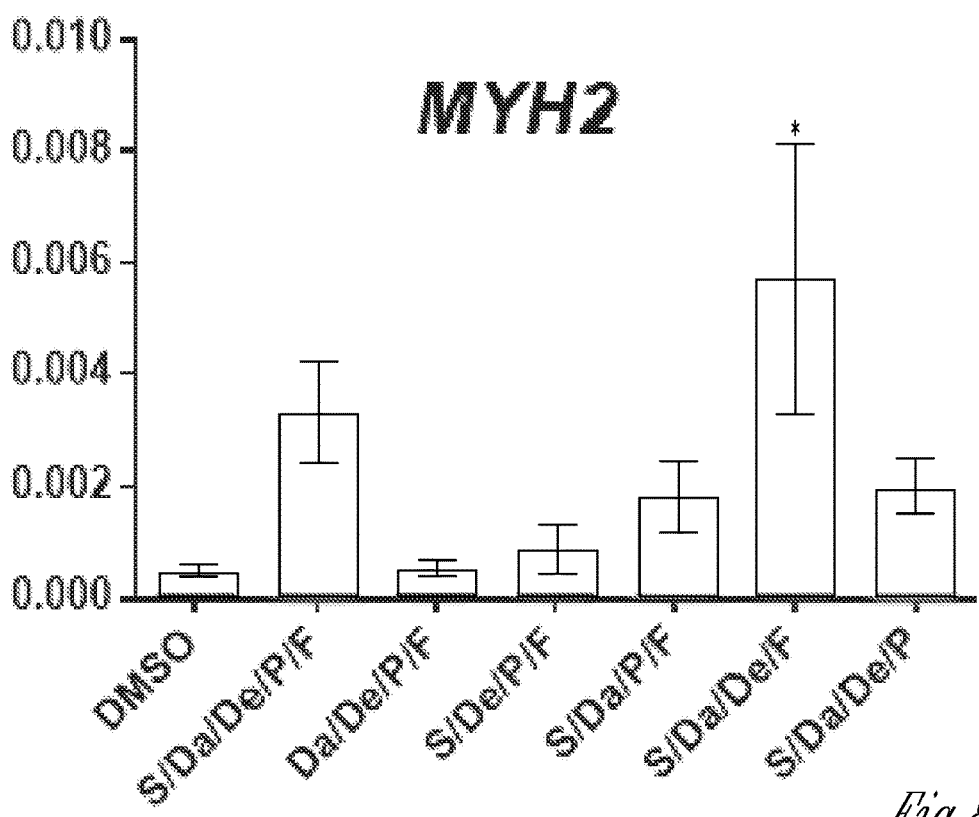
Figures 5, 8E:
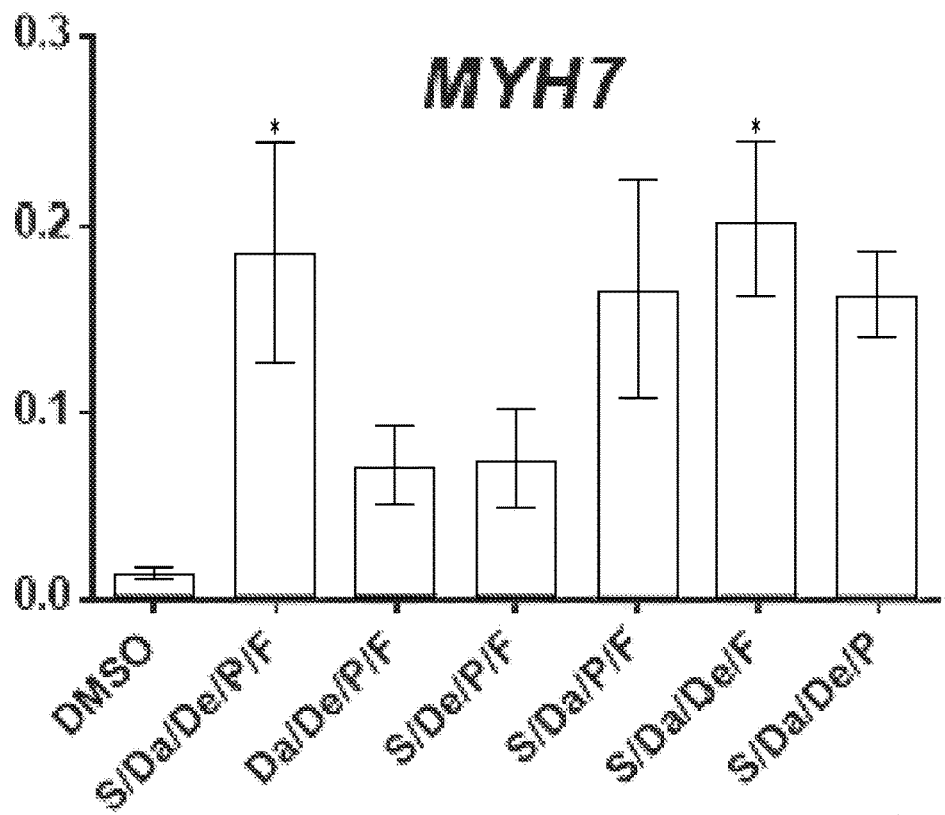
Figures 6, 8E:
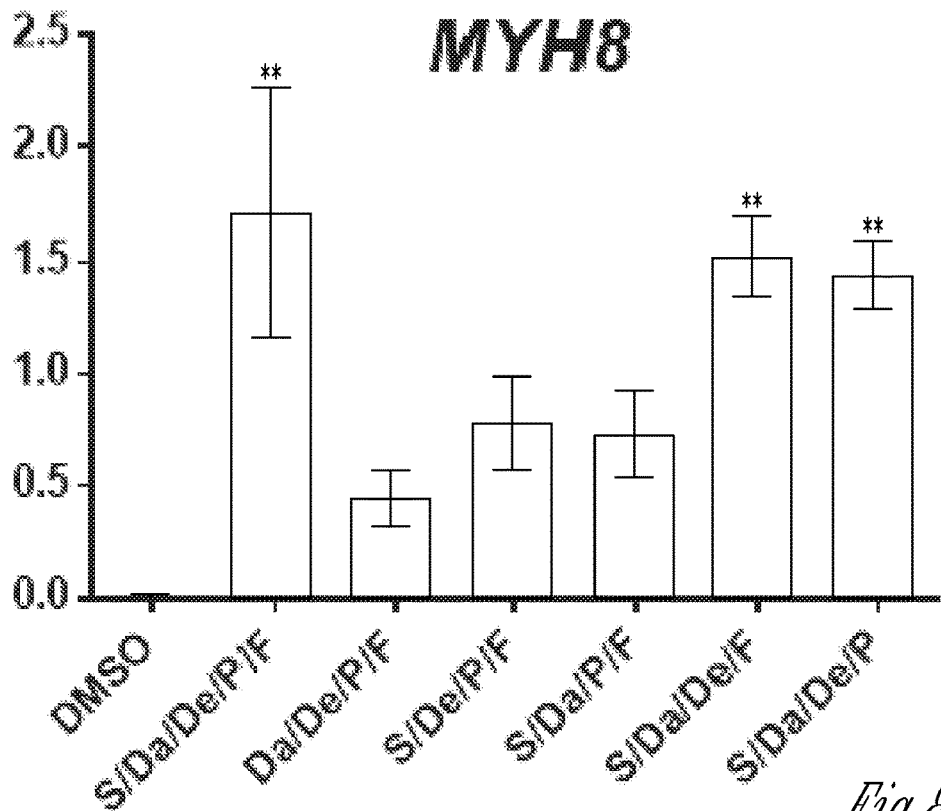
Figures 1, 9A:
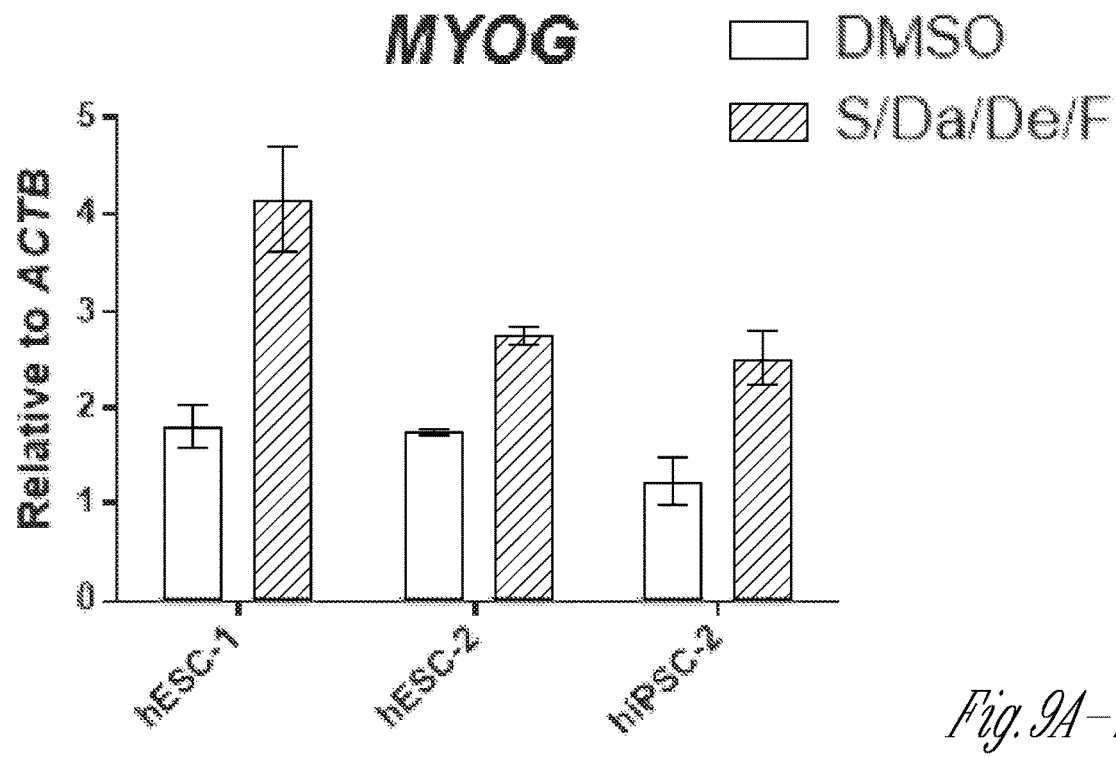
FIGS. 9A-B. Addition of SB 431542, DAPT, Dexamethasone and Forskolin (S/Da/De/F) during the terminal differentiation of myotubes derived from pluripotent stem cell lines (hESC-1, hiPSC1 and hiPSC-2) induces myotubes maturation in vitro. (A) Myogenin and MyHC profile (MYH2, MYH3, MYH7 and MYH8) expression analysis of hESC-1, hiPSC-1 or hiPSC-2-derived myotubes treated with S/Da/De/F during terminal differentiation. Data are shown as mean±SEM. *p<0.05, p<0.01, *p<0.001. (B) Western blot analysis for the expression of neonatal MyHC and Desmin in hESC-1, hiPSC-1 or hiPSC-2-derived myotubes treated with S/Da/De/F during terminal differentiation. B-Actin was used as loading control.
Figures 2, 9A:
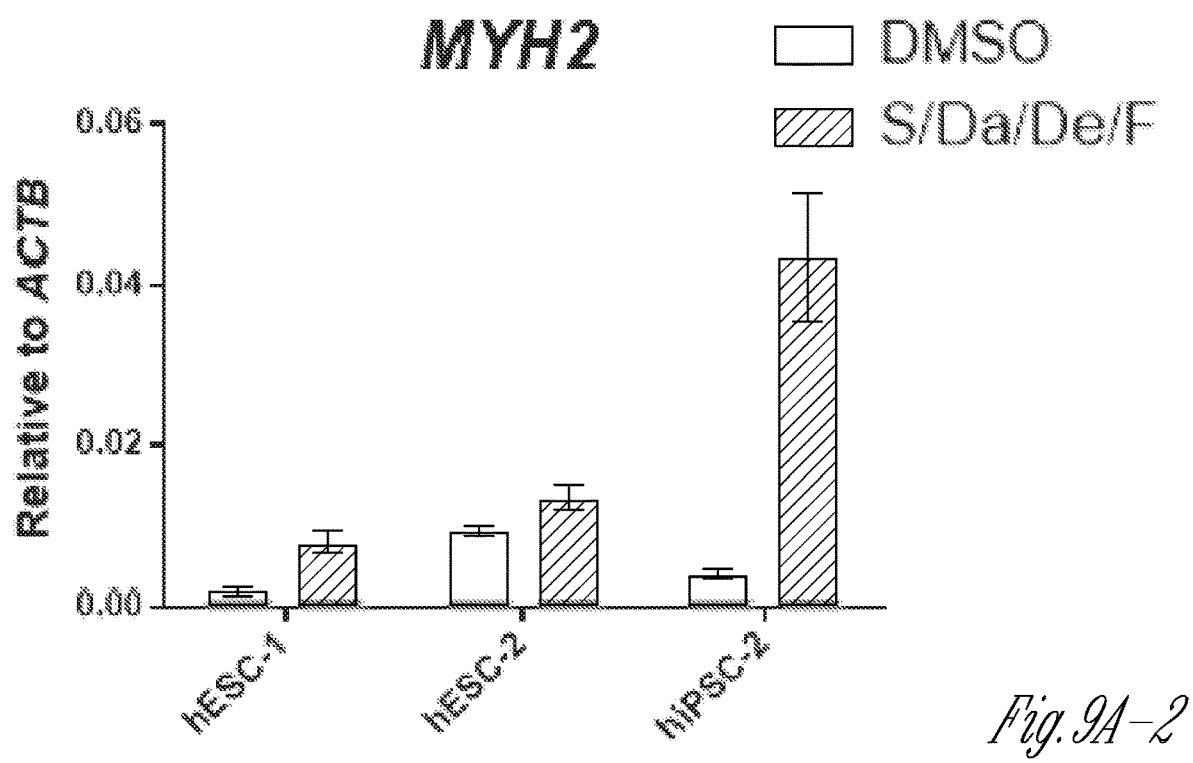
Figures 3, 9A:
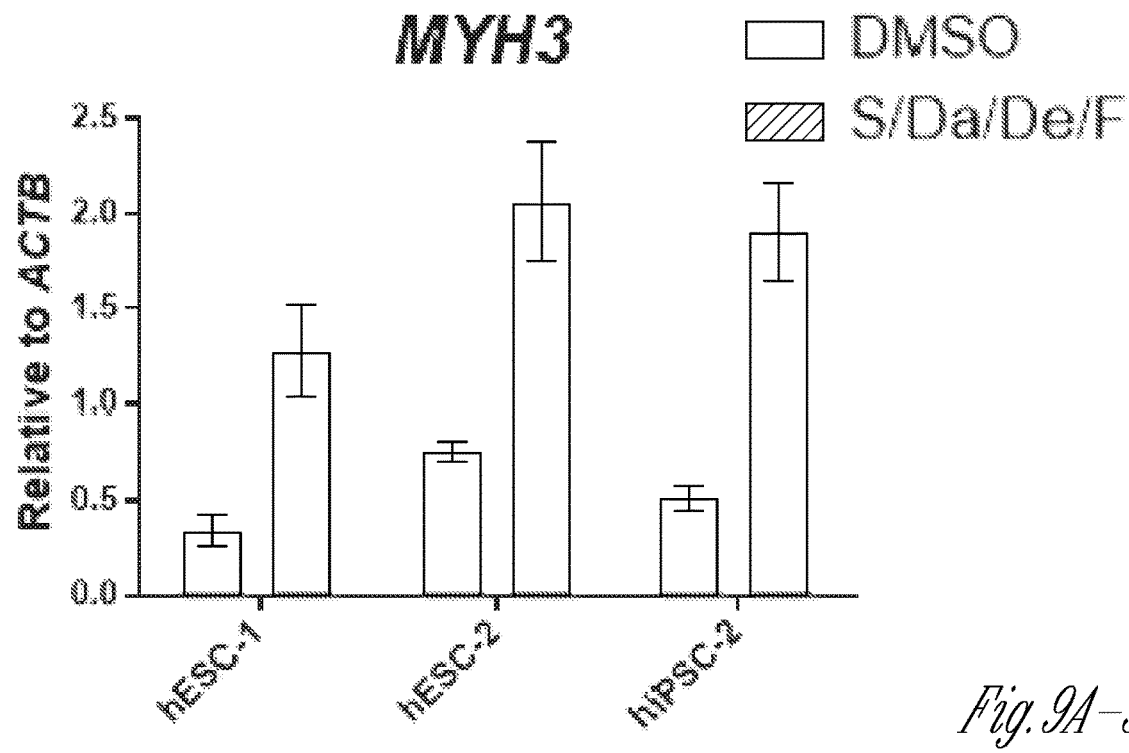
Figures 4, 9A:
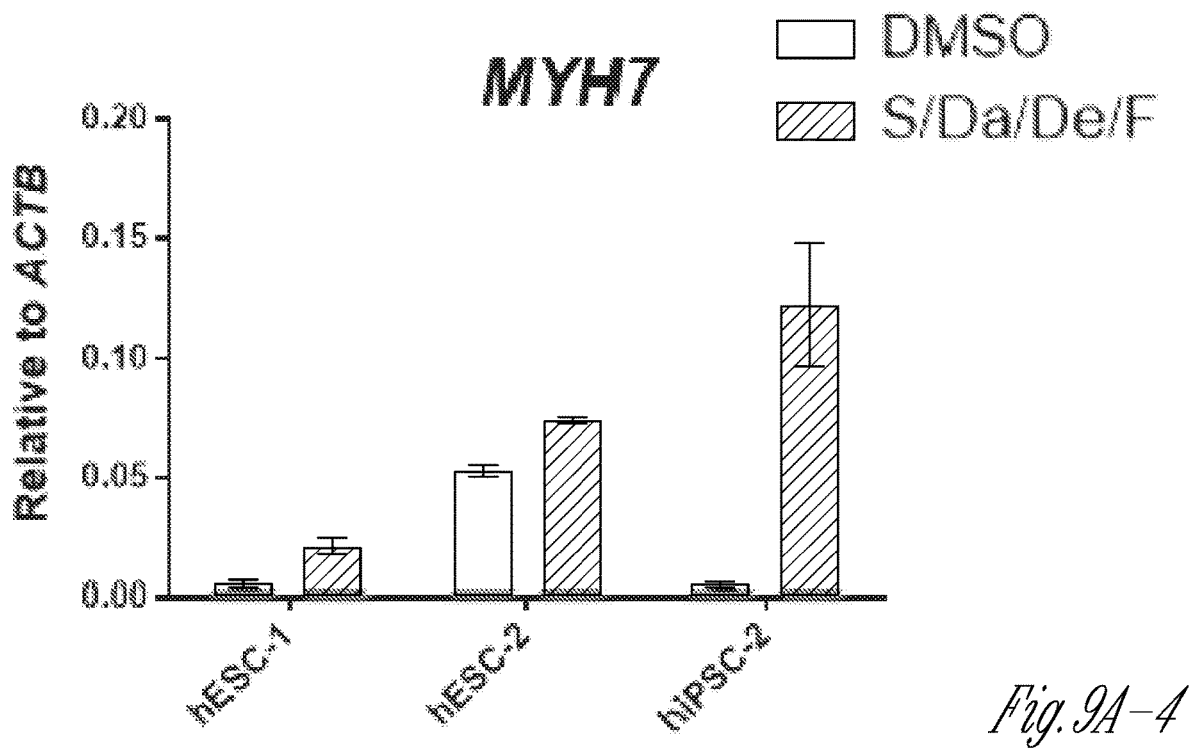
Figures 5, 9A:
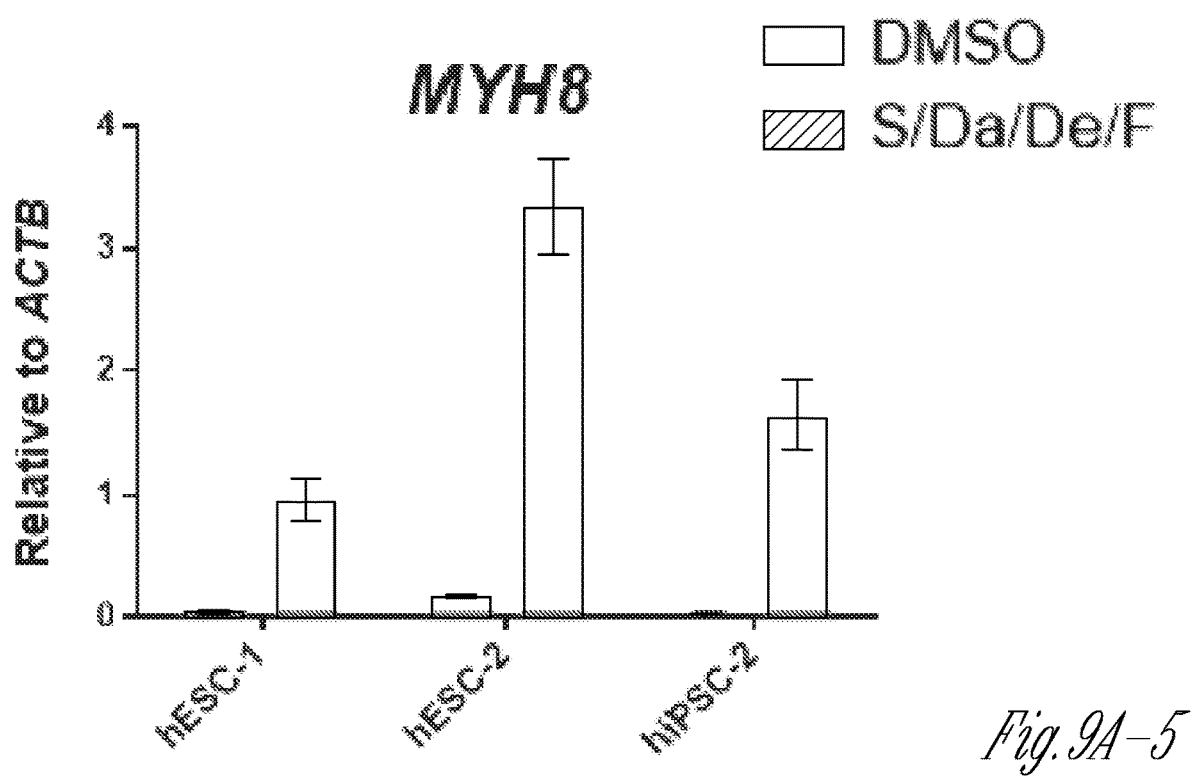
Figure 9B:
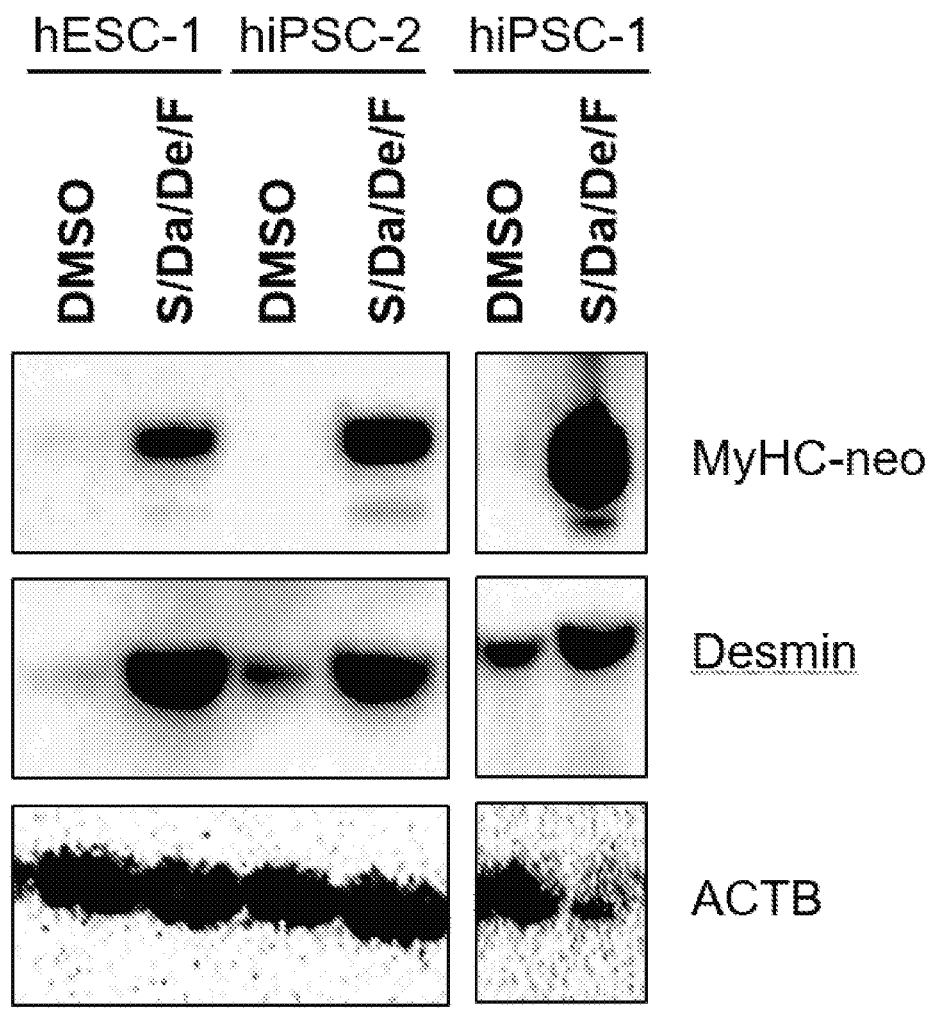
Figure 10A:
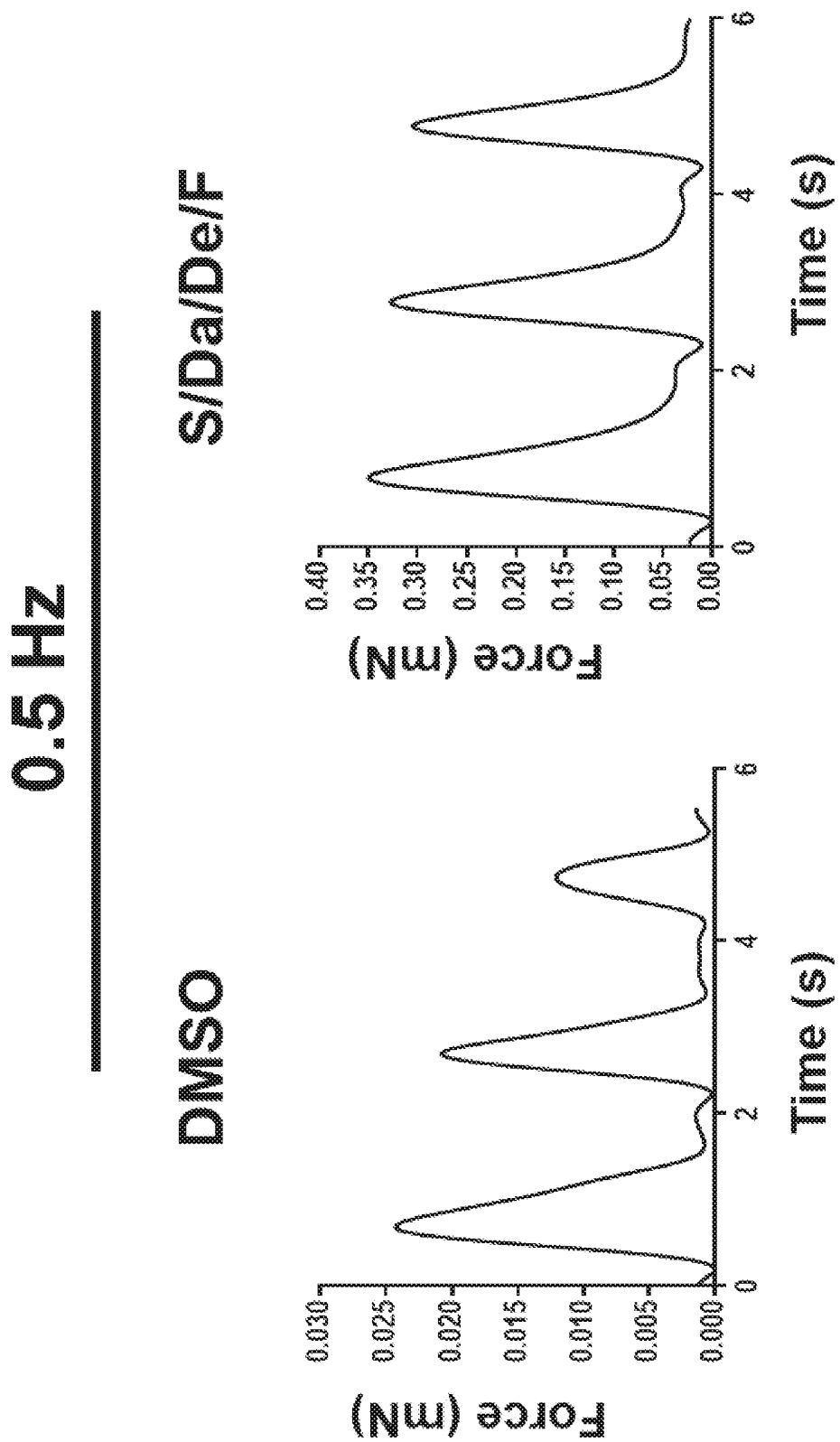
FIGS. 10A-E. Contractile force generation and gene expression of muscle constructs. (A), (B) Representative twitch and tetanic force patterns, respectively, generated by constructs differentiated in the presence and absence of S/Da/De/F. (C) Substantial increase of the twitch force at 0.5 Hz when the differentiation medium contained S/Da/De/F. (D) Substantial increase of the tetanic force at 20 Hz when the differentiation medium contained S/Da/De/F. (E) Analysis of myogenic gene expression suggests S/Da/De/F enhanced myogenic differentiation. (Each construct was differentiated for five days. For each condition, 3 constructs were examined. For each construct, 9 twitch peaks and 3 tetanic measurements were used for analysis).
Figure 10B:
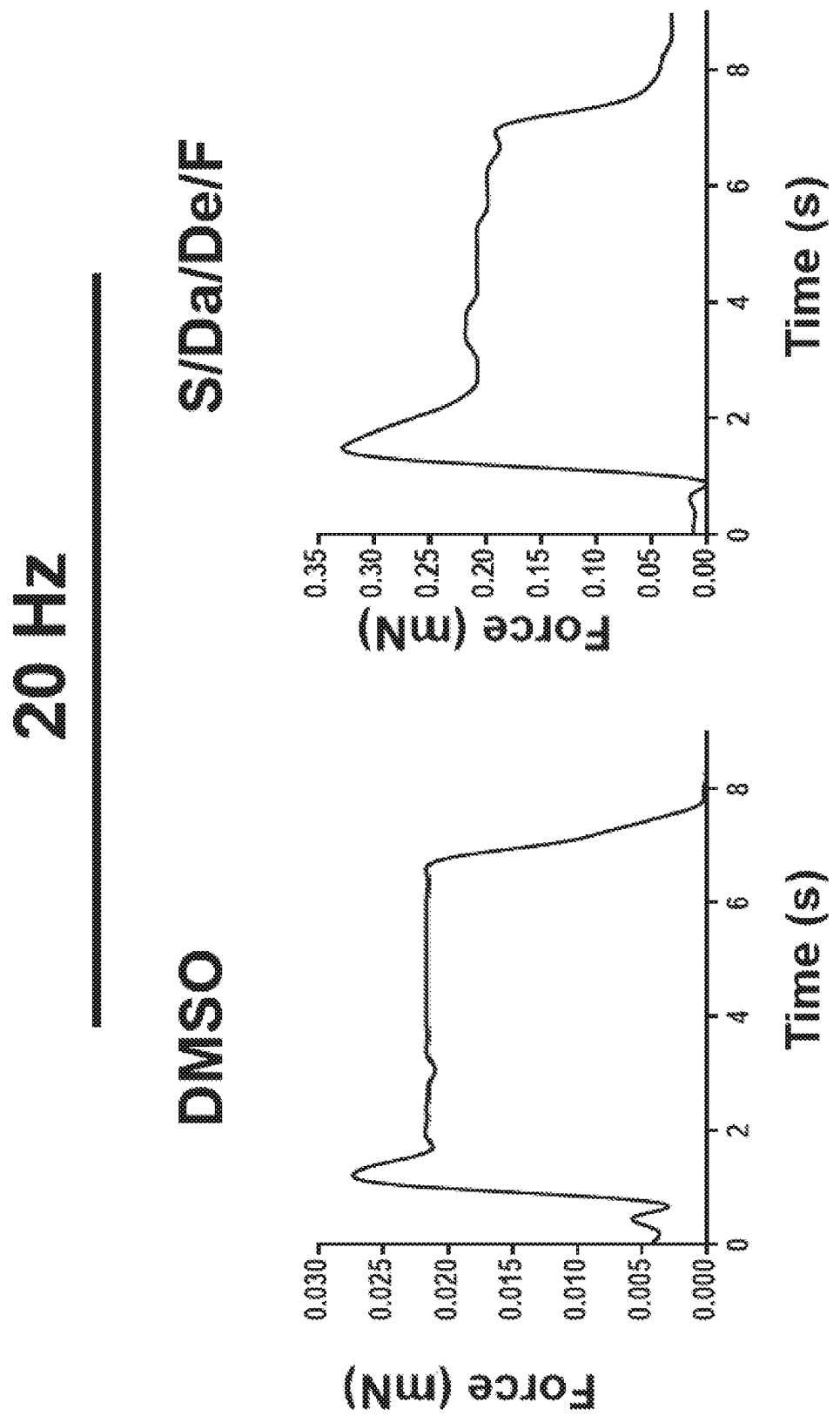
Figure 10C:
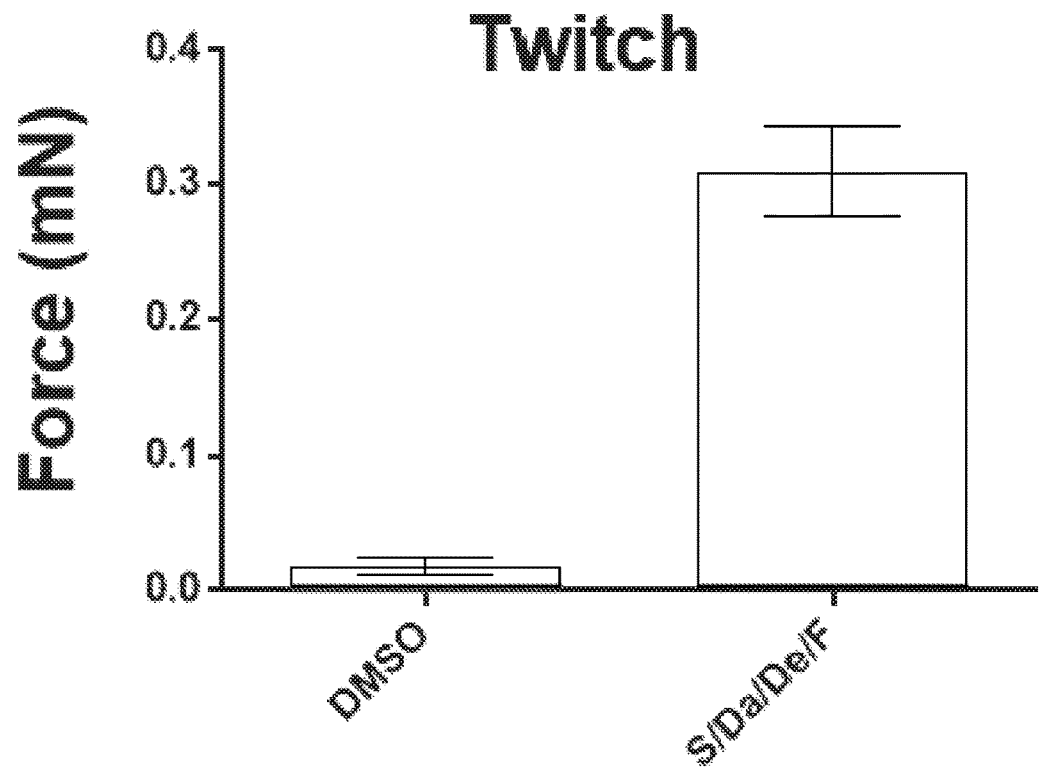
Figure 10D:
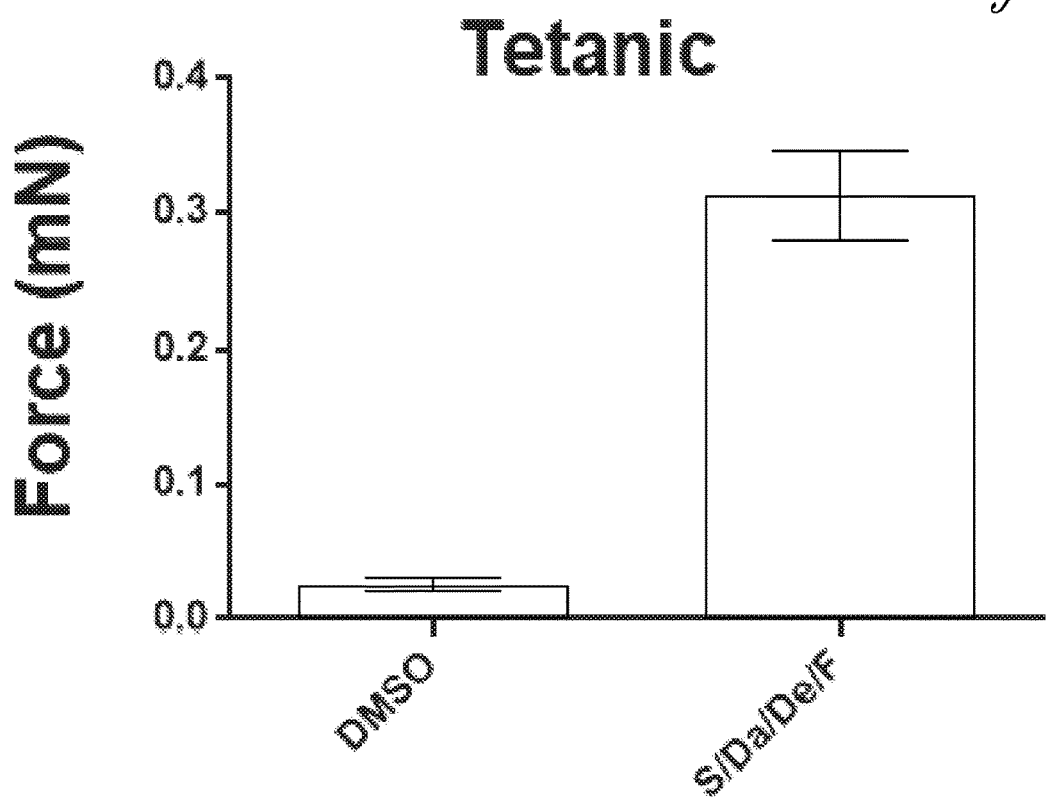
Figures 1, 10E:
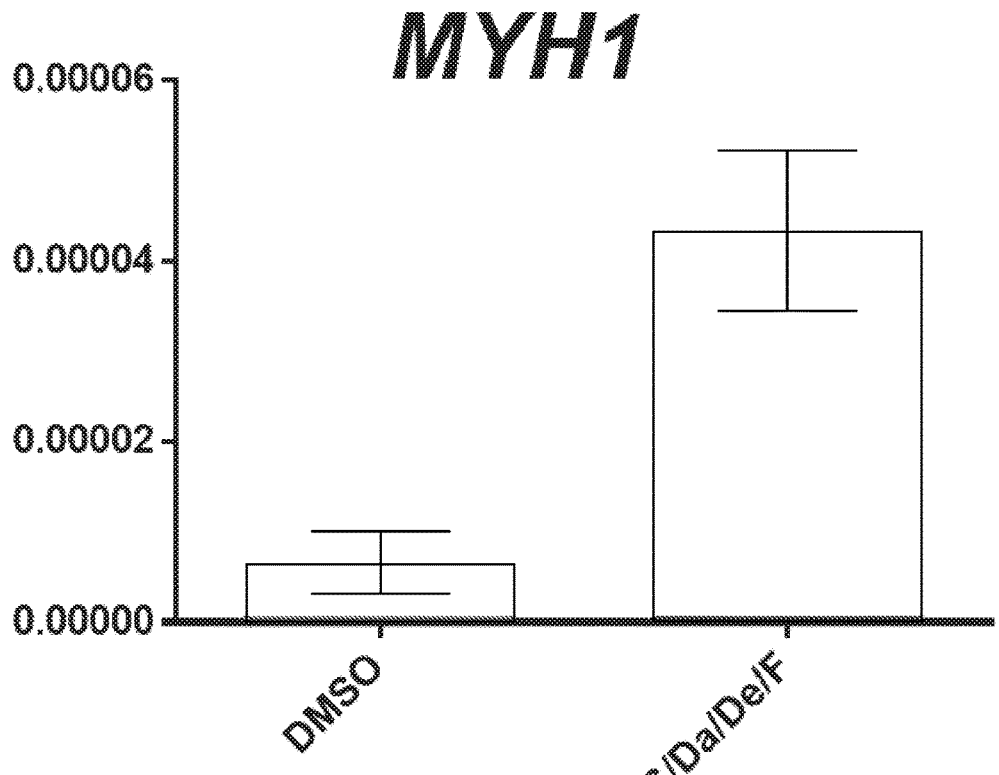
Figures 2, 10E:
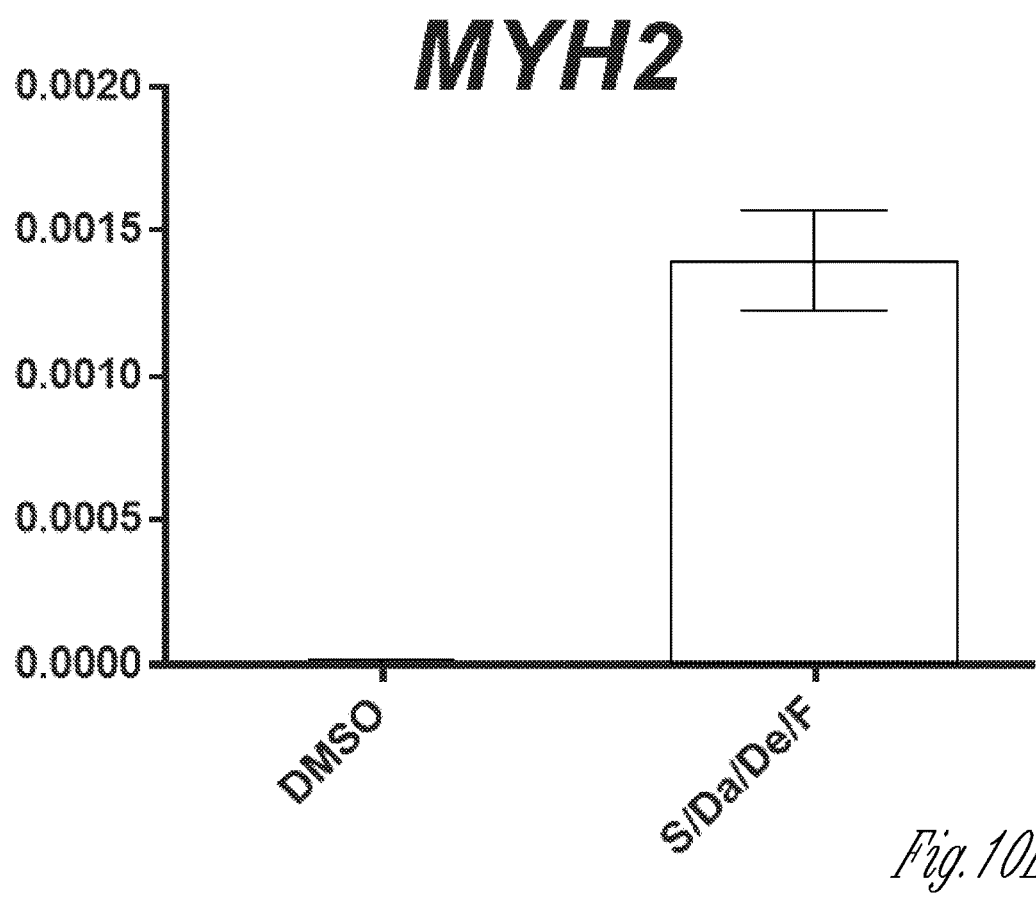
Figures 3, 10E:
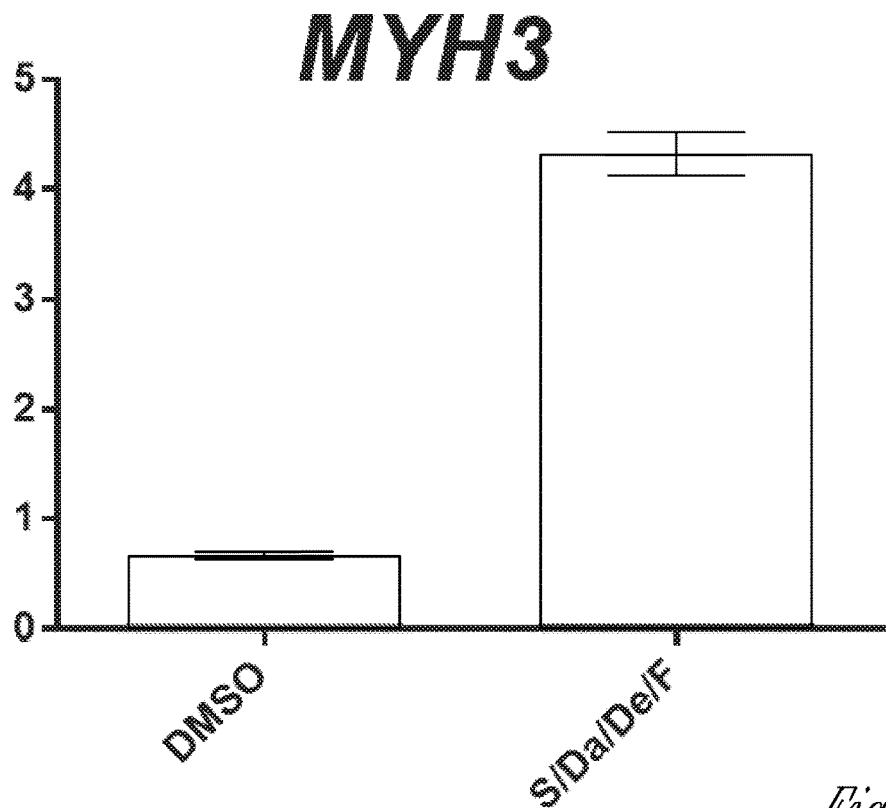
Figures 4, 10E:
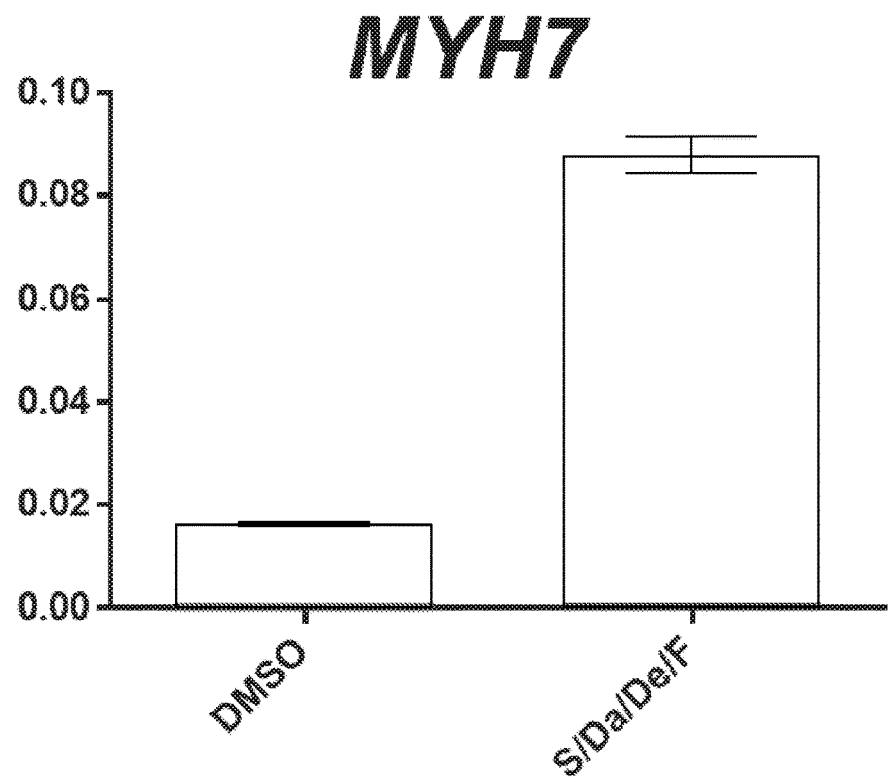
Figures 5, 10E:
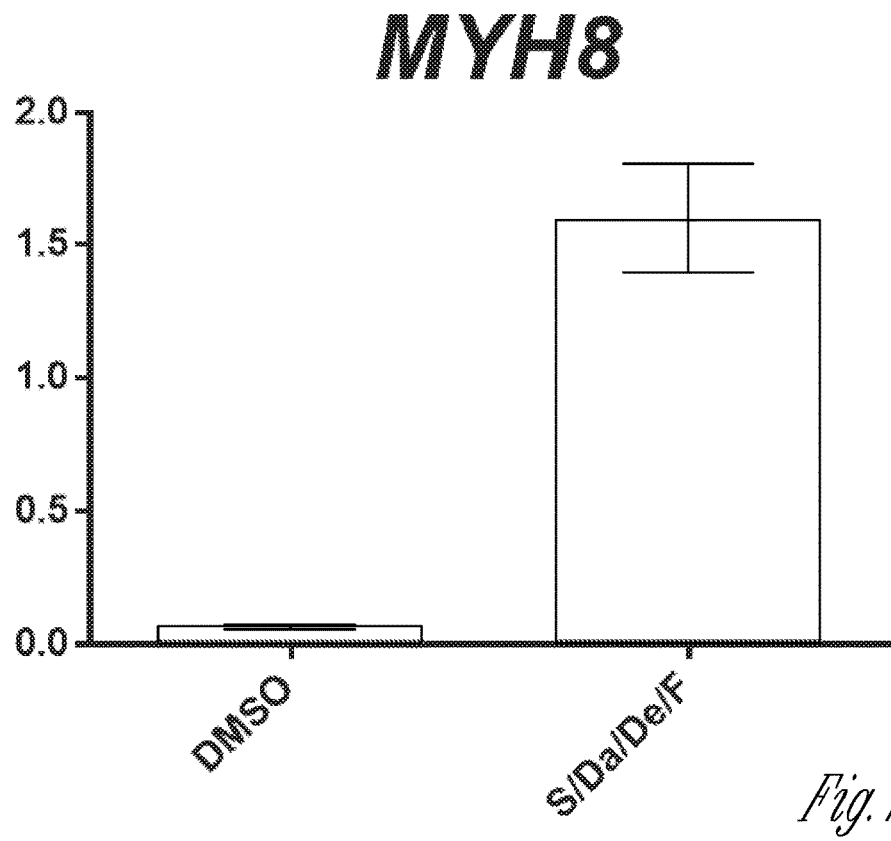
Figures 6, 10E:
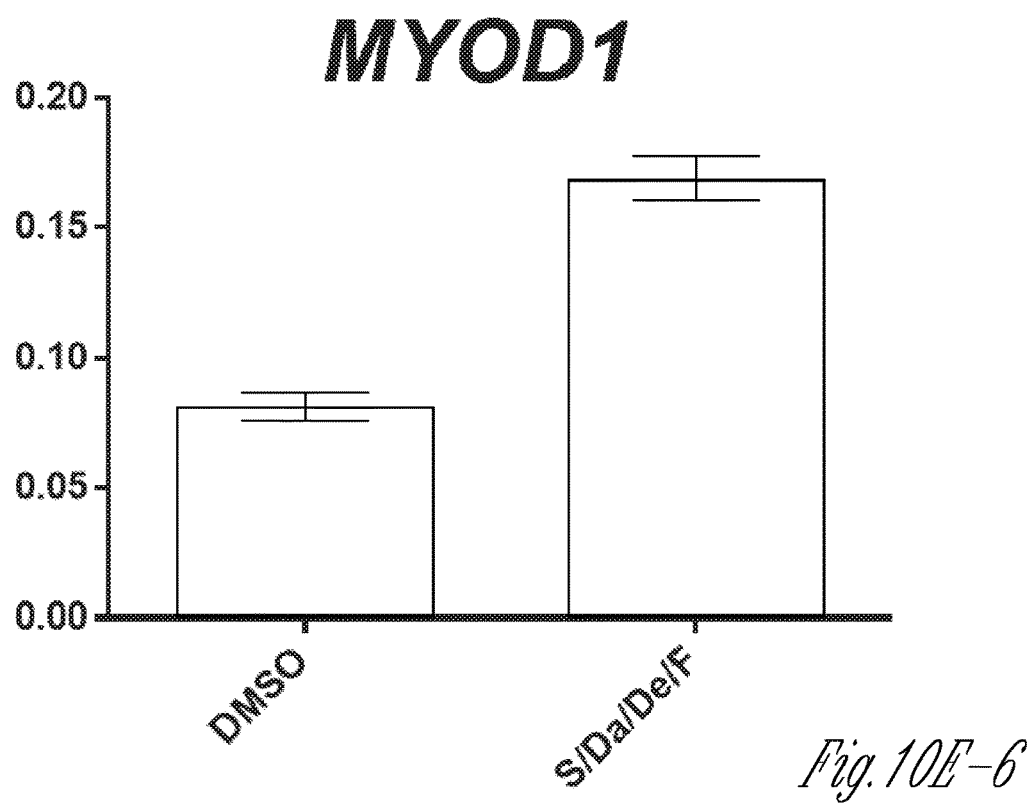
Figures 7, 10E:
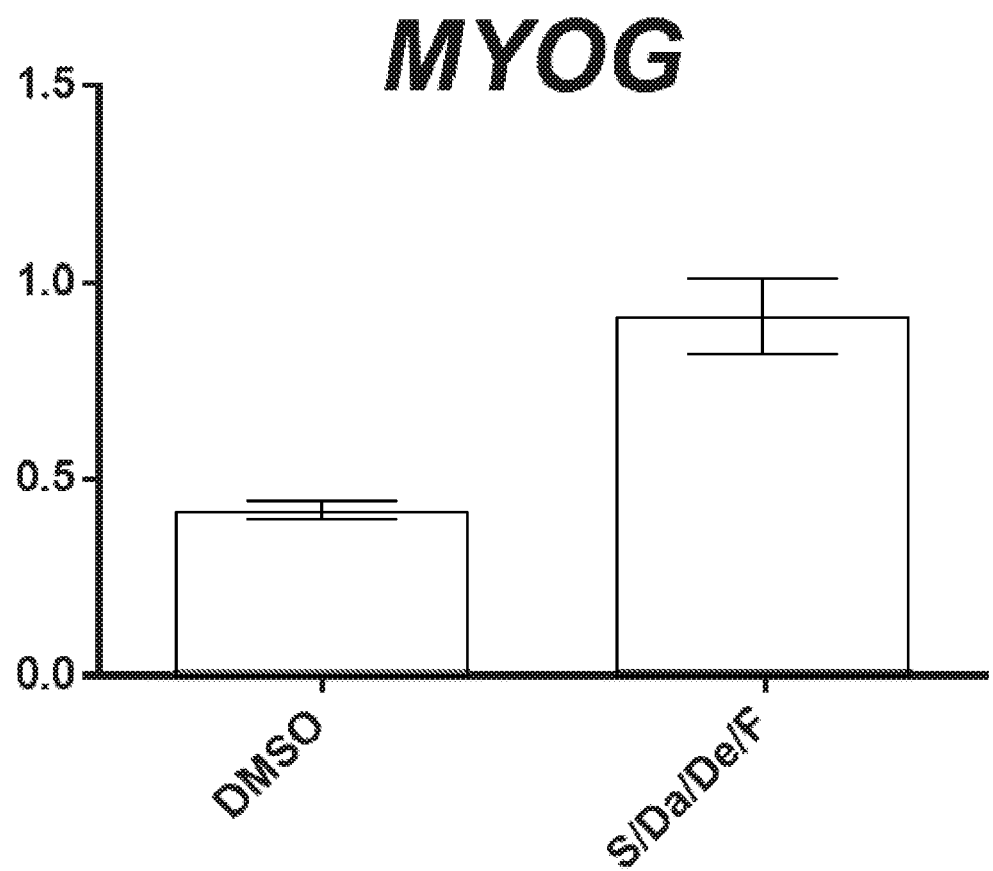

Primary skeletal myoblasts stand as the current gold standard for in vitro modeling of skeletal muscle diseases. However, isolation of patient-specific myoblasts requires a muscle biopsy, which is an invasive and uncomfortable procedure for patients. Patient-specific pluripotent stem cell skeletal muscle derivatives represent an attractive potential alternative for in vitro disease modeling without the requirement of muscle biopsy. The technology of reprogramming somatic cells into induced pluripotent stem (iPS) cells offers tremendous potential for the generation of large amounts of lineage-committed cells for disease modeling, as well as other applications, including drug screening. Nevertheless, variations on the myogenic differentiation efficiency among cell lines, as well as the overall embryonic nature of iPS cell-derivatives (across lineages) stands as a barrier for reliable disease modeling studies. In order to address these issues, the Embryoid body (EB)-iPAX7 myogenic differentiation protocol was modified to incorporate inhibition of BMP and TGFβ signaling, which has been shown to promote somite-like formation along the myogenic specification from pluripotent stem cells. Modification of the protocol resulted in myogenic progenitors with improved in vitro differentiation to myotubes while showing efficient in vivo engraftment capabilities upon intramuscular transplantation (FIG. 6). Then, to overcome the of lack of maturation, a small molecule library screening using Tocriscreen Stem Cell Toolbox was used to identify small molecule compounds that could promote maturation of iPS derived myotubes. Five different small molecule compounds were identified from this screening which promoted higher myotube differentiation efficiency: DAPT (Da), SB 431542 (S), Dexamethasone (De), PD 0325901 (P) and Forskolin (F), (FIG. 7). Upon treatment with a combination of four out of the five identified small molecule compounds (S/Da/De/F), the myotube differentiation and fusion enhanced dramatically (FIG. 8). And these myotubes also express, at RNA and protein levels, the markers of maturation which were almost absent without treatment (FIG. 9). In addition, this treatment also enhances the force generation of 3-dimensional myobundles derived from iPS myogenic progenitors in response to electrical stimulus which indicates functional maturation (FIG. 10). Thus, small molecule compounds have been identified which can enhance the maturation of iPS derived myotubes and these myotubes can be utilized for modeling various skeletal muscle diseases in vitro.

Materials and Methods

Cell Culture and Myogenic Differentiation of PS Cells

ES and iPS cells were maintained in mTeSR1 medium (stemcell technologies) on Matrigel coated plates. ES/iPS cells were dissociated with Accumax and passaged once they reach 90% confluency and plated with 10 μM ROCK inhibitor, Y-27632 (Tocris). To induce conditional expression of PAX7, ES/iPS cells were co-transduced with lentiviral vectors, pSAM2-iPAX7-IRES-GFP and FUGW-rtTA to generate iPAX7 cells (Darabi et al, 2012). For myogenic differentiation, 1 million iPAX7-ES/iPS cells were plated with 10 μM Y-27632 in a 60-mm petri dish and incubated for 2 days in a 60-rpm shaker at 37° C. to derive embryoid bodies. Cells were then switched to myogenic medium (MM) supplemented with 10 μM GSK3β inhibitor (CHIR 990217, tocris). Myogenic medium consisted of IMDM basal medium supplemented with 15% fetal bovine serum, 10% horse serum, 1% penicillin/streptomycin, 1% glutamax, 1% KOSR, 50 μg/ml ascorbic acid, 4.5 mM monothioglycerol. After 2 days, cells were switched to MM with 200 nM BMP inhibitor (LDN-193189, cayman chemical) and 10 μM TGF-β inhibitor (SB-431542, cayman chemical), (+LS), or vehicle (−LS). 24 hours later, the medium was supplemented with 1 μg/ml Doxycyline (dox).

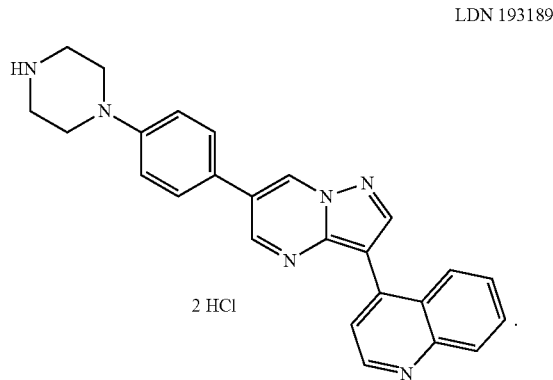 [SMILES: c1ccc2c(-c3cnn4cc(-c5ccc(N6CCNCC6)cc5)cnc34)ccnc2c1]

LDN 193189

After 24 hours, cells were switched to MM with 1 μg/ml Doxycyline and incubated at 37° C. for 2 days. 1/10th of EBs were then plated on gelatin coated T-75 flasks in MM with 1 μg/ml dox and 5 ng/ml human basic fibroblast growth factor (bFGF). After 4 days, cells were dissociated with 0.25% trypsin-EDTA, FACS sorted for GFP to derive myogenic progenitors which were plated at a density of 2 million/T-75 flask in MM with 1 μg/ml dox and 5 ng/ml bFGF. Once the cells reached 90% confluency, myogenic progenitors were dissociated with 0.25% trypsin-EDTA and passaged at a ratio of 1:6 to 1:8. To induce terminal differentiation, myogenic progenitors at P3-4 were plated at a density of 75,000 cells/24-well plate and allowed to grow confluent for 3 days. The medium was then switched to low nutrient differentiation medium (DM) consisting of DMEM-KO supplemented with 20% KOSR, 1% NEAA, 1% glutamax and 1% penicillin-streptomycin and incubated for five days to derive myotubes.

Transplantation Experiment

Human iPS cell-derived myogenic progenitors were transplanted in 6-week old NSG mice from Jackson labs. 24 hours before transplantation, tibialis anterior muscle was injured with 15 μl of 10 μM cardiotoxin (CTX). Following day, myogenic progenitors at P3 were dissociated with enzyme free cell dissociation buffer (Gibco) and resuspended in PBS at a density of 1 million cells/15 μl. CTX injured TA muscle was transplanted with 1 million cells. 6 weeks post transplantation, TA muscles were collected and frozen in OCT. Frozen muscles were cryosectioned to make sections at a thickness of 10 μm. Immunofluorescence staining of the tissue sections was performed using antibodies specific to human dystrophin (MANDYS106, Millipore) and human lamin A/C (Abcam). Stained sections were imaged in Zeiss upright microscope and the number of fibers that stain double positive for human dystrophin and lamin A/C were quantified.

Small Molecule Library Screening

Small molecule library screening was done using the tocriscreen stem cell toolbox kit (tocris) which consisted of 80 compounds. Myogenic progenitors at passage P3 or P4 were seeded at 12,000 cells/well in 96-well plates (triplicates) and incubated at 37° C. for 3 days to reach 100% confluency. After 3 days, the cells were switched to DM supplemented with 10 μM of the compounds from the library or with DMSO. Cells were incubated in this differentiation medium for 5 days to derive myotubes. Cells were then fixed with 4% PFA and stained for MHC and DAPI. The stained plates were imaged using cytation plate reader and 49 pictures were taken per well to cover most of the area. The images were stitched together and the ratio of area of MHC/DAPI staining was quantified using Image J and normalized to that of DMSO treated cells. 5 compounds which showed an increase of 1.2-fold or more in ratio of MHC/DAPI relative to DMSO were used for further studies. Different combinations were made with selected compounds and their effect on differentiation was tested and quantified.

Immunofluorescence Staining

For the immunofluorescence staining, cells were fixed with 4% PFA for 20-30 mins at RT which was followed by permeabilization with 0.3% Triton X-100 in PBS for 20 mins at RT. Cells were then blocked with 3% BSA in PBS for 1 hour. Primary antibody diluted in 3% BSA was added after blocking and was incubated overnight at 4° C. Following this incubation, cells were washed with PBS and incubated with secondary antibody and DAPI for 45-60 mins at RT in dark. After this incubation, cells were washed with PBS and stored in dark at 4° C. until imaging. For the staining of tissues, the frozen sections were allowed dry at RT for 15 mins and the sections were rehydrated in PBS for 5 mins. Following this, fixation was performed with 4% PFA for 10 mins. The rest of the staining protocol was similar to that of the cells. After the secondary antibody incubation and washing, the slides were mounted with coverslips using ProLong Gold Antifade Mountant with DAPI. The stained sections were imaged using Zeiss upright microscope.

Western Blotting

Protein extraction was performed using lysis buffer consisting of 20 mM Tris HCl, 0.1 mM EDTA, 1 mM DTT, 20 μg/ml soybean trypsin inhibitor, 28 μM E64 and 2 mM PMSF supplemented with 1× Laemmli sample buffer. Cells were scraped in the lysis buffer and the lysate was boiled at 95° C. for 10 mins. The total protein concentration of the lysate was quantified using Bradford assay. 100 μg of total protein was electrophoresed in 7.5% SDS-PAGE gel. The proteins were transferred on to immobilon PVDF membrane (Millipore). The blot was blocked with 5% dry milk in TBST for 1 hour at RT. After blocking, the blot was incubated with primary antibody diluted in 5% BSA in TBST overnight at 4° C. Following this incubation, the blot was washed three times with TBST and then incubated with HRP conjugated secondary antibody. After three washes with TBST, the protein detection was performed using Pierce ECL or Supersignal west chemiluminescent substrate (Thermofisher). The chemiluminescence signal was captured in X-ray film or using chemidoc imager (Biorad).

Antibodies Used for Immunofluorescence and Western Blot

| Antibody | Manufacturer | Catalog number |
|---|---|---|
| Myosin heavy chain | DSHB | MF20 |
| Human dystrophin | DSHB | MANDYS106 |
| Human Lamin A + C | Abcam | ab108595 |
| Titin | DSHB | 9 D10 |
| Alexa fluor 555 goat anti-mouse IgG | ThermoFisher | A-21424 |
| Alexa fluor 488 goat anti-rabbit IgG | ThermoFisher | A-11008 |
| MHC-neo | DSHB | N3.36 |
| Desmin | SCBT | sc-23879 |
| ACTB | SCBT | sc-4778 |
| Amersham ECL Mouse IgG, HRP-linked | GE healthcare | NA931 |

RNA Isolation and Quantitative RT-PCR

Cells were lysed using Trizol reagent (Thermofisher) and the RNA extraction was performed using purelink RNA mini kit (Thermofisher) with on-column DNAse treatment as per manufacturer's instructions. RNA concentration was quantified using Nanodrop. For quantitative RT-PCR analysis, reverse transcription was performed using Superscript Vilo cDNA synthesis kit (Thermofisher) as per manufacturer's instruction, qPCR was performed using taqman probes (Applied Biosystems) and Premix Ex Taq probe qPCR kit (Takara). For each qPCR reaction in 384-well plate, cDNA amount corresponding to 10 ng of total RNA, 0.5 µl of taqman probe and 5 µl of 2× master mix was utilized. QPCR was performed using QuantStudio 6 Flex Real-Time PCR System and the Ct values were determined. $C_t$ value for gene of interest was normalized to that of the house keeping control using the $2^{\wedge}$-delta $C_t$ calculation and compared between the treated and untreated groups.

Generation of 3D Muscle Constructs and Force Measurement

Three-dimensional muscle constructs were generated in home-made culture wells having dimensions of 15 mm×5 mm×5 mm (length×width×depth), with each well containing two posts near the ends of the well. A suspension of hiPSC-derived myogenic progenitors (10 million cells/mL, passage 4) was prepared in a solution containing 6 mg mL-1 bovine fibrinogen (Sigma), 1-unit bovine thrombin (Sigma), and 10% (v/v) growth factor reduced Matrigel (R&D), and the suspension was quickly pipetted into the culture wells, followed by gelation at 37° C. for 1 hour. All constructs were cultured in the myogenic expansion medium for 3 days, followed by differentiation for 5 days in the KOSR medium supplemented with S/Da/De/F (dissolved in DMSO at 10 µM each). Controls in which the KOSR differentiation medium containing the same amount of DMSO (0.4% v/v) were conducted. On day 3 of differentiation, 25% of the medium was replaced with the fresh medium. All the media were supplemented with 2 mg/mL ε-aminocaproic acid (Sigma) to prevent fibrin degradation.

Contractile forces generated by the constructs in response to electrical stimulation at 0.5 Hz (twitch) or 20 Hz (tetanus) were measured on a custom-built apparatus after five days of differentiation1. In brief, a construct was maintained at 37° C., and the two ends were mounted on two pins, one of which was adjustable and connected to a force transducer (Harvard Apparatus, 60-2994 model). Prior to measurements, the construct was stretched by 20% of its initial length with the adjustable pin. Electrical pulses were generated with a cardiac stimulator (Astro-Med Inc., S88× Model, 10 ms pulse width) at a frequency of 0.5 or 20 Hz for 6 seconds. Contractile forces were recorded with a custom program in LabView, and the data were analyzed with a custom code in MATLAB. For each twitch peak or tetanic plateau, the maximum force was used for analysis. The construct was then treated with TRI Reagent® (Sigma) for further qPCR analysis. For each differentiation condition, three constructs were quantitatively examined.

BIBLIOGRAPHY

Barberi, T., et al. (2007). Derivation of engraftable skeletal myoblasts from human embryonic stem cells. Nat Med 13, 642-648.

Borchin, B., et al. (2013). Derivation and FACS-mediated purification of PAX3+/PAX7+ skeletal muscle precursors from human pluripotent stem cells. Stem Cell Reports 1, 620-631.

Shelton, M., et al. (2014). Derivation and expansion of PAX7-positive muscle progenitors from human and mouse embryonic stem cells. Stem Cell Reports 3, 516-529.

Young, Courtney S., et al. (2016). A single CRISPR-Cas9 deletion strategy that targets the majority of DMD patients restores dystrophin function in hiPSC-derived muscle cells. Cell Stem Cell 18, 533-540.

Chal, J., and Pourquié. (2017). Making muscle: skeletal myogenesis in vivo and in vitro. Development 144, 2104-2122.

Darabi, R., et al. (2012). Human ES- and iPS-derived myogenic progenitors restore DYSTROPHIN and improve contractility upon transplantation in dystrophic mice. Cell Stem Cell 10, 610-619.

Darabi, R., and Perlingeiro, R. C. (2016). Derivation of Skeletal Myogenic Precursors from Human Pluripotent Stem Cells Using Conditional Expression of PAX7. Methods Mol Biol 1357, 423-439.

Dovey, H. F., et al. (2001). Functional γ-secretase inhibitors reduce β-amyloid peptide levels in brain. J. Neurochem. 76, 173-181.

Gavai A V, et al. 2015. Discovery of clinical candidate BMS-906024: A potent Pan-Notch inhibitor for the treatment of Leukemia and Solid tumors. ACS Med Chem Lett 6, 523-527.

Kim J., et al., (2017) "Expansion and Purification Are Critical for the Therapeutic Application for Pluripotent Stem Cell-Derived Myogenic Progenitors" Stem Cell Reports, 9:12-22. PMID: 28528701.

Xi, H. et al. In Vivo Human Somitogenesis Guides Somite Development from hPSCs. Cell reports 18, 1573-1585, doi:10.1016/j.celrep. 2017.01.040 (2017).

Black, L. D., 3rd, et al. Cell-induced alignment augments twitch force in fibrin gel-based engineered myocardium via gap junction modification. Tissue Eng Part A 15, 3099-3108, (2009).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An in vitro method of obtaining myotubes comprising:
   (a) differentiating pluripotent stem cells into myogenic progenitors;
   (b) terminally differentiating said myogenic progenitors from (a) into mature myotubes in the presence of a combination of DAPT (Da), SB-431542 (S), dexamethasone (De) and forskolin (F); and
   (c) isolating said myotubes.

2. The method of claim 1, wherein the pluripotent stem cells are human induced pluripotent stem cells (hiPSC) or embryonic stem cells (hESC).

3. The method of claim 2, wherein the mature myotubes have increased expression of MHC8.

4. The method of claim 1, wherein the pluripotent stem cells are genetically modified.

5. The method of claim 1, wherein the (a) differentiating pluripotent stem cells to myogenic progenitors is carried out by inducible expression of PAX7.

6. An in vitro method to increase the efficiency of myotube generation and maturation from pluripotent stem cells comprising:
   (a) differentiating pluripotent stem cells to myogenic progenitors; and
   (b) terminally differentiating said myogenic progenitors from (a) into mature myotubes in the presence of a combination of DAPT (Da), SB-431542 (S), dexamethasone (De) and forskolin (F),
   wherein myotube maturation is increased in the presence of a combination of DAPT (Da), SB-431542 (S), dexamethasone (De) and forskolin (F), as compared to maturation in the absence of a combination of DAPT (Da), SB-431542 (S), dexamethasone (De) and forskolin (F).

7. An in vitro method to generate myotubes comprising:
   (a) differentiating pluripotent stem cells into myogenic progenitors; and
   (b) terminally differentiating said myogenic progenitors from (a) into mature myotubes in the presence of a combination of DAPT (Da), SB-431542 (S), dexamethasone (De) and forskolin (F).

8. A composition comprising myogenic progenitors, DAPT (Da), SB-431542 (S), dexamethasone (De) and forskolin (F).

* * * * *

UNITED STATES PATENT AND TRADEMARK OFFICE
CERTIFICATE OF CORRECTION

PATENT NO. : 11,697,798 B2
APPLICATION NO. : 16/770917
DATED : July 11, 2023
INVENTOR(S) : Perlingeiro et al.

It is certified that error appears in the above-identified patent and that said Letters Patent is hereby corrected as shown below:

In the Drawings

Figure 6C:
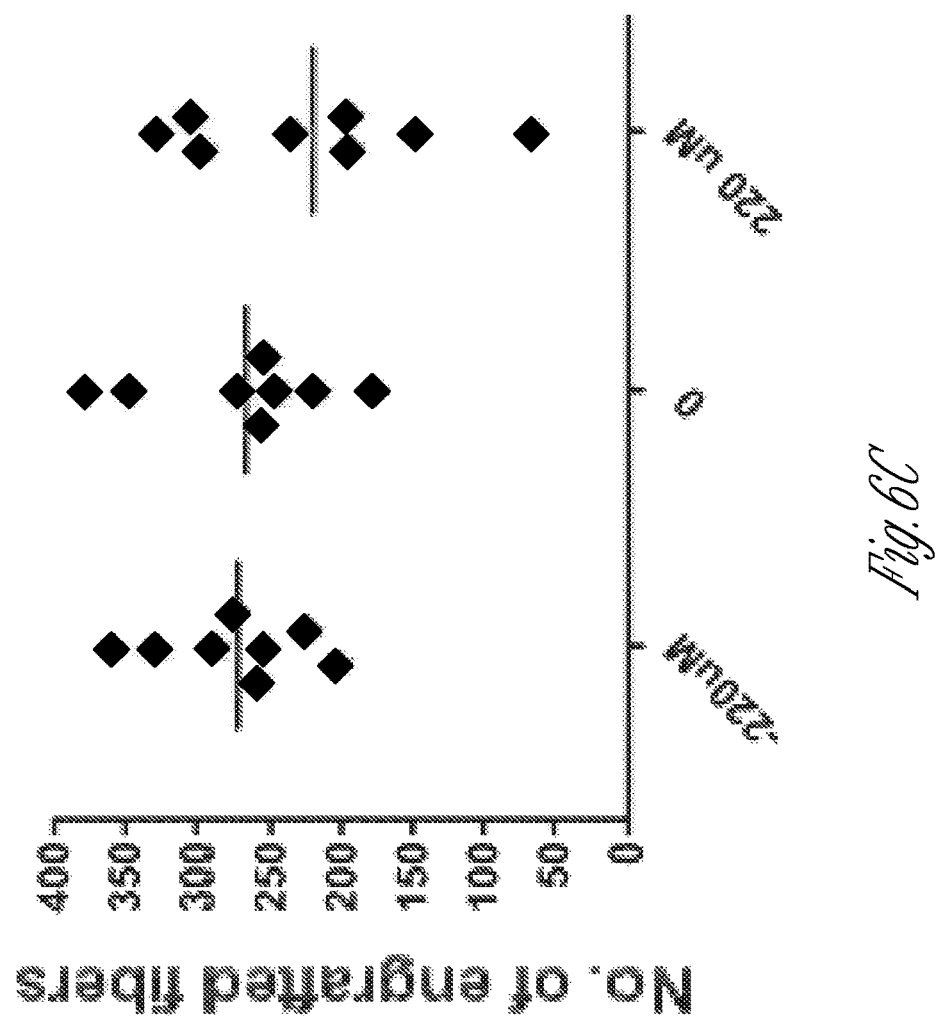
Figure 6B:
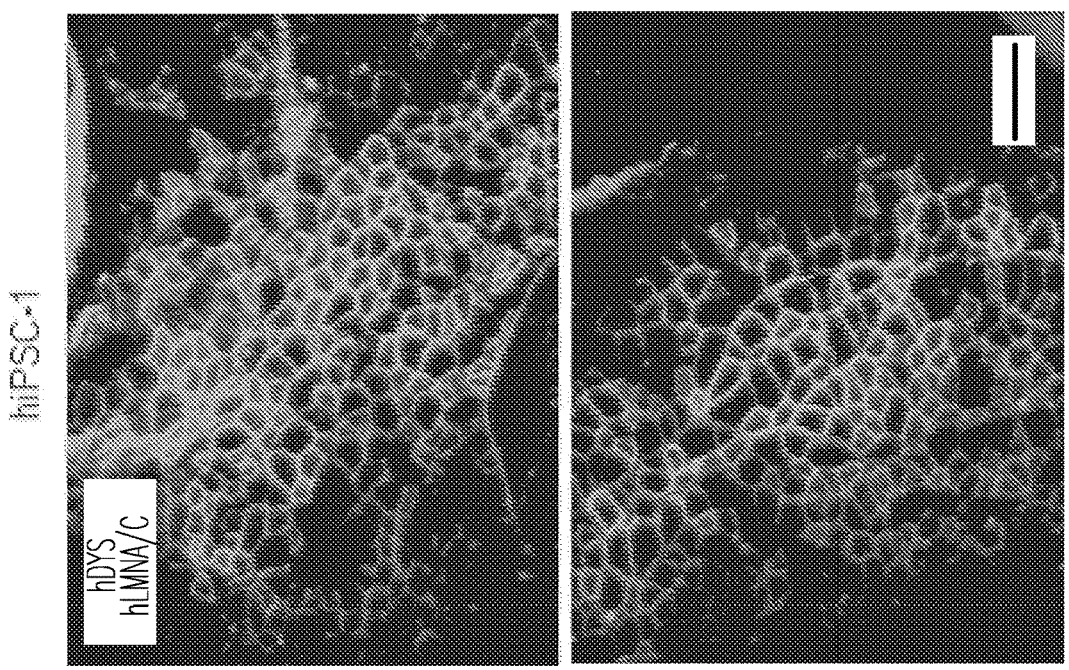

Sheet 8 of 29, Fig. 6C, delete "–220uM" and insert -- –220 µM-- therefor

On sheet 8 of 29, Fig. 6C, delete "220 uM" and insert --220 µM-- therefor

In the Specification

In Column 1, Line 10, delete "Jun. 2," and insert --Jun. 20,-- therefor

In Column 4, Line 20, delete "hiPSC1" and insert --hiPSC-1-- therefor

In Column 8, Line 66, delete "phenyl)glycine" and insert --phenylglycine-- therefor In Column 10, Line 34, delete "to." and insert --to,-- therefor In Column 12, Line 52, delete "uM" and insert --µM-- therefor In Column 12, Line 55, delete "uM" and insert --µM-- therefor In Column 12, Line 55, delete "uM" and insert --µM-- therefor In Column 12, Line 59, delete "ug/ml" and insert --µg/ml-- therefor In Column 12, Line 65, delete "ug/ml" and insert --µg/ml-- therefor In Column 13, Line 1, delete "ug/ml" and insert --µg/ml-- therefor In Column 13, Line 5, delete "uM" and insert --µM-- therefor Signed and Sealed this
Eleventh Day of June, 2024

Katherine Kelly Vidal
*Director of the United States Patent and Trademark Office*

CERTIFICATE OF CORRECTION (continued)
U.S. Pat. No. 11,697,798 B2

In Column 13, Line 5, delete "uM" and insert --µM-- therefor

In Column 13, Line 23, delete "ug" and insert --µg-- therefor

In Column 13, Line 45, delete "TaMan" and insert --TaqMan-- therefor

In Column 14, Line 1, delete "uM" and insert --µM-- therefor

In Column 14, Line 1, delete "uM" and insert --µM-- therefor

In Column 17, Line 32, delete "instruction," and insert --instruction.-- therefor In Column 17, Line 38, delete "Ct" and insert --$C_t$-- therefor In Column 18, Line 2, delete "differentiation1." and insert --differentiation.-- therefor